United States Patent
Pilarski

(10) Patent No.: US 7,137,951 B2
(45) Date of Patent: Nov. 21, 2006

(54) METHOD OF FOOD AND INSULIN DOSE MANAGEMENT FOR A DIABETIC SUBJECT

(76) Inventor: Joseph Pilarski, 15 Wertheim Court, Suite 404, Richmond Hill, Ontario (CA) L4B 3H7

( * ) Notice: Subject to any disclaimer, the term of this patent is extended or adjusted under 35 U.S.C. 154(b) by 31 days.

(21) Appl. No.: 10/691,145

(22) Filed: Oct. 22, 2003

(65) Prior Publication Data

US 2004/0180810 A1    Sep. 16, 2004

Related U.S. Application Data

(60) Provisional application No. 60/420,289, filed on Oct. 23, 2002, provisional application No. 60/498,580, filed on Aug. 29, 2003.

(30) Foreign Application Priority Data

Oct. 23, 2002   (CA)   .................................. 2409374

(51) Int. Cl.
*A61B 5/00*   (2006.01)
(52) U.S. Cl. ...................... 600/300; 128/922
(58) Field of Classification Search .............. 600/300, 600/301, 365; 128/920, 921, 923; 702/19; 235/375; 604/65–67
See application file for complete search history.

(56) References Cited

U.S. PATENT DOCUMENTS

| | | | | |
|---|---|---|---|---|
| 5,216,597 A | * | 6/1993 | Beckers | ........................ 356/39 |
| 5,420,108 A | | 5/1995 | Shohet | |
| 5,997,475 A | * | 12/1999 | Bortz | ........................ 600/300 |
| 6,543,682 B1 | * | 4/2003 | Glaser | ........................ 235/66 |
| 6,691,043 B1 | * | 2/2004 | Ribeiro, Jr. | ................... 702/19 |
| 2002/0107476 A1 | * | 8/2002 | Mann et al. | ................... 604/67 |
| 2003/0040821 A1 | * | 2/2003 | Case | ........................ 700/90 |

FOREIGN PATENT DOCUMENTS

EP   0834825   8/1998

OTHER PUBLICATIONS

Joseph Pilarski and Eugenio Angueira. "Don't Spill the Sugar." 1997-2003 Grasshopper Middleware Inc., distributed by elife Publications Inc. Published Nov. 2002.
B. Madrick. "Carbohydrate Counting." Http/www.diabetes.ca, updated May 2002, pp. 1-3.
National Diabetes Information Clearinghouse (NDIC). "Diabetes Control and Complications Trial (DCCT)." Http://diabetes.niddk.nih.gov, NIH Publication No. 02-3874, Oct. 2001 pp. 1-5.
J. M. Lachin et al. "The Diabetes Control and Complications Trial (DCCT)." http://www.bsc.gwu.edu, pp. 1-3.
"More details about the DCCT." Http://www.faqs.org, last update Mar. 16, 2004, pp. 1-3.

* cited by examiner

*Primary Examiner*—Max F. Hindenburg
*Assistant Examiner*—Patricia Mallari
(74) *Attorney, Agent, or Firm*—Synnestvedt & Lechner LLP

(57)   ABSTRACT

The invention relates to a method of food and insulin dose management for a diabetic subject, comprising:
  providing an intended insulin unit value or an intended carbohydrate unit value representing the amount of insulin or carbohydrate intended for intake by the subject; and
  determining the balance value of either insulin units or carbohydrate units needed to balance with the provided unit value and maintain blood sugar in the subject in a target blood sugar range.

17 Claims, 68 Drawing Sheets

FIG. 1

Figure 31A:
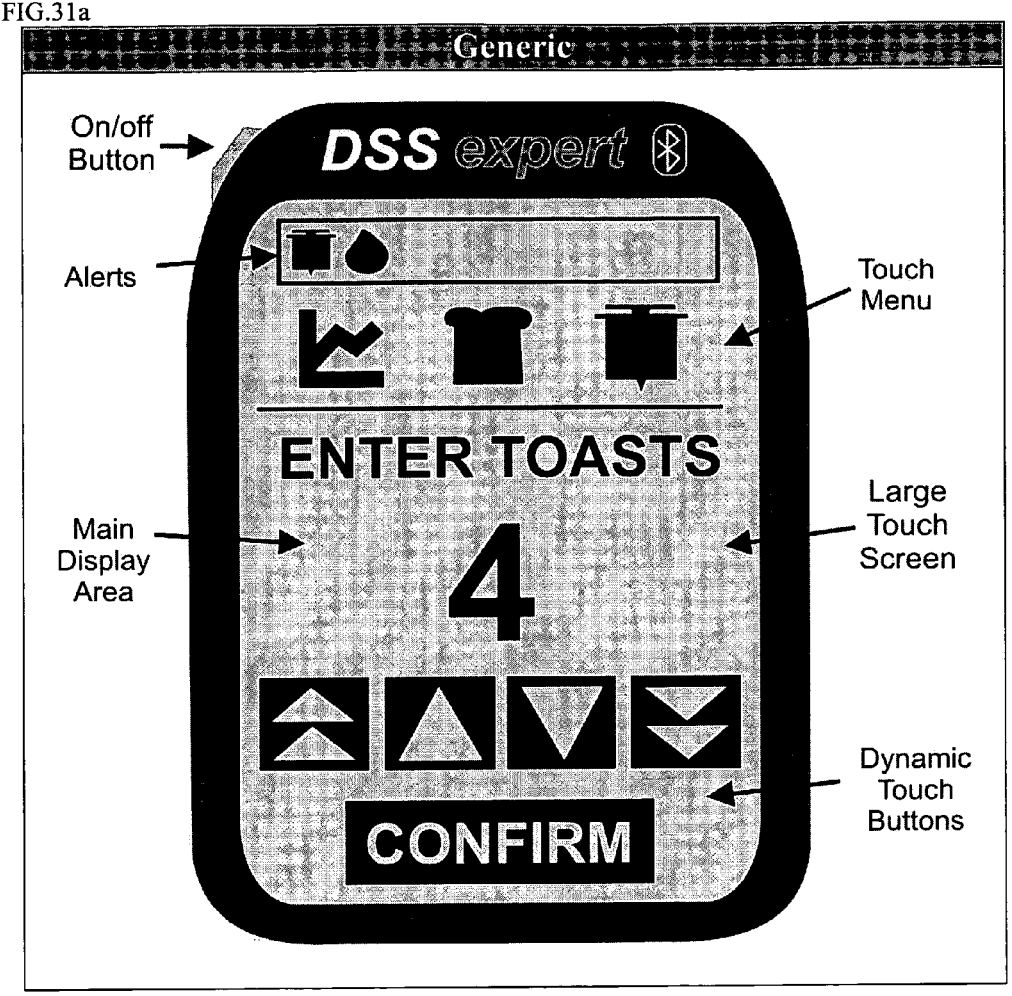

| Time | Starting Sugar | Toasts | Meal 1 | 2 | Total | Insulin | Dose 1 | 2 | 3 | Total | Ending Sugar |
|---|---|---|---|---|---|---|---|---|---|---|---|
| 8:00 am | 144 | 2 +108 | +108 | | +108 | ?‑108 | ‑108 | | | | 144 |
| 9:00 am | 144 | | | | | | | | | | 144 |

FIG 2

| Time | Starting Sugar | Toasts | Meal 1 | Meal 2 | Total | Insulin | Dose 1 | Dose 2 | Dose 3 | Total | Ending Sugar |
|---|---|---|---|---|---|---|---|---|---|---|---|
| 8:00 am | 144 | 2 +108 | +108 | | +108 | 4 -108 | | | | | 252 |
| 9:00 am | 252 | | | | | | -54 | | | -54 | 198 |
| 10:00 am | 198 | | | | | | -54 | | | -54 | 144 |
| 11:00 am | 144 | | | | | | | | | | 144 |

FIG. 3

| Time | Starting Sugar | Toasts | Meal | | | Insulin | Dose | | | Ending Sugar |
|---|---|---|---|---|---|---|---|---|---|---|
| | | | 1 | 2 | Total | | 1 | 2 | 3 Total | |
| 8:00 am | 144 | 2 +108 | +108 | | +108 | 16 -432 | -432 | | -432 | -180 |

FIG. 4

| Time | Starting Sugar | Toasts | Meal 1 | Meal 2 | Total | Insulin | Dose 1 | Dose 2 | Dose 3 | Total | Ending Sugar |
|---|---|---|---|---|---|---|---|---|---|---|---|
| 8:00 am | 144 | 2 +108 | +36 | | +36 | 16 -432 | | | | | 180 |
| 9:00 am | 180 | | +36 | | +36 | | | | | | 216 |
| 10:00 am | 216 | | +36 | | +36 | | -27 | | | -27 | 225 |
| 11:00 am | 225 | | | | | | -27 | | | -27 | 198 |
| 12:00 pm | 198 | | | | | | -27 | | | -27 | 171 |
| 1:00 pm | 171 | | | | | | -27 | | | -27 | 144 |
| 2:00 pm | 144 | | | | | | -27 | | | -27 | 117 |
| 3:00 pm | 117 | | | | | | -27 | | | -27 | 90 |

FIG. 5

| Time | Starting Sugar | Toasts | Meal 1 | Meal 2 | Meal Total | Insulin | Dose 1 | Dose 2 | Dose 3 | Dose Total | Ending Sugar |
|---|---|---|---|---|---|---|---|---|---|---|---|
| 6:00 am | 144 | | | | | | | | | | 144 |
| 7:00 am | 144 | | | | | | | | | | 144 |
| 8:00 am | 144 | 2 +108 | +36 | | | 16 -432 | -27 | | | -27 | 153 |
| 9:00 am | 153 | | +36 | | | | -27 | | | -27 | 162 |
| 10:00 am | 162 | | +36 | | | | -27 | | | -27 | 171 |
| 11:00 am | 171 | | | | | | -27 | | | -27 | 144 |
| 12:00 pm | 144 | | | | | | -27 | | | -27 | 117 |
| 1:00 pm | 117 | | | | | | -27 | | | -27 | 90 |

FIG.6

| Time | Starting Sugar | Toasts | Meal 1 | Meal 2 | Total | Insulin | Dose 1 | Dose 2 | Dose 3 | Total | Ending Sugar |
|---|---|---|---|---|---|---|---|---|---|---|---|
| 8:00 am | 144 | | | | | | | | | | 144 |
| 9:00 am | 144 | | | | | | | | | | 144 |
| 10:00 am | 144 | 2 +108 | +36 | | +36 | 16 -432 | -27 | | | -27 | 153 |
| 11:00 am | 153 | | +36 | | +36 | | -27 | | | -27 | 162 |
| 12:00 pm | 162 | | +36 | | +36 | | -27 | | | -27 | 171 |
| 1:00 pm | 171 | | | | | | -27 | | | -27 | 144 |
| 2:00 pm | 144 | | | | | | -27 | | | -27 | 117 |
| 3:00 pm | 117 | | | | | | -27 | | | -27 | 90 |

FIG. 7

| Time | Starting Sugar | Toasts | Meal 1 | Meal 2 | Total | Insulin | Dose 1 | Dose 2 | Dose 3 | Total | Ending Sugar |
|---|---|---|---|---|---|---|---|---|---|---|---|
| 8:00 am | 144 | | | | | 16 -432 | | | | | 144 |
| 9:00 am | 144 | 1 +54 | +18 | | +18 | | | | | | 162 |
| 10:00 am | 162 | | +18 | | +18 | | -27 | | | -27 | 153 |
| 11:00 am | 153 | | +18 | | +18 | | -27 | | | -27 | 144 |
| 12:00 pm | 144 | 1 +54 | +18 | | +18 | | -27 | | | -27 | 135 |
| 1:00 pm | 135 | | +18 | | +18 | | -27 | | | -27 | 126 |
| 2:00 pm | 126 | | +18 | | +18 | | -27 | | | -27 | 117 |
| 3:00 pm | 117 | | | | | | -27 | | | -27 | 90 |

FIG. 8A

| Time | Starting Sugar | Toasts | Meal 1 | Meal 2 | Meal Total | Insulin | Dose 1 | Dose 2 | Dose 3 | Dose Total | Ending Sugar |
|---|---|---|---|---|---|---|---|---|---|---|---|
| 8:00 am | | 1 | | | | | | | | | |
| 9:00 am | | | | | | | | | | | |
| 10:00 am | | 1 | | | | | | | | | |
| 11:00 am | | | | | | | | | | | |
| 12:00 pm | | 3 | | | | | | | | | |
| 1:00 pm | | | | | | | | | | | |
| 2:00 pm | | 1 | | | | | | | | | |
| 3:00 pm | | | | | | | | | | | |

FIG. 8B

| Time | Starting Sugar | Toasts | Meal 1 | Meal 2 | Meal Total | Insulin | Dose 1 | Dose 2 | Dose 3 | Total | Ending Sugar |
|---|---|---|---|---|---|---|---|---|---|---|---|
| 4:00 pm | | 1 | | | | | | | | | |
| 5:00 pm | | | | | | | | | | | |
| 6:00 pm | | 3 | | | | | | | | | |
| 7:00 pm | | | | | | | | | | | |
| 8:00 pm | | 1 | | | | | | | | | |
| 9:00 pm | | | | | | | | | | | |
| 10:00 pm | | | | | | | | | | | |
| 11:00 pm | | | | | | | | | | | |

FIG. 9A

| Time | Starting Sugar | Toasts | Meal 1 | Meal 2 | Meal Total | Insulin | Dose 1 | Dose 2 | Dose 3 | Total | Ending Sugar |
|---|---|---|---|---|---|---|---|---|---|---|---|
| 8:00 am | | 1 +54 | | | | 1 -297 | | | | | |
| 9:00 am | | | | | | | | | | | |
| 10:00 am | | 1 +54 | | | | | -32.5 | | | -32.5 | |
| 11:00 am | | | | | | | -32.5 | | | -32.5 | |
| 12:00 pm | | 3 +162 | | | | | -32.5 | | | -32.5 | |
| 1:00 pm | | 1 +54 | | | | | -32.5 | | | -32.5 | |
| 2:00 pm | | | | | | | -32.5 | | | -32.5 | |
| 3:00 pm | | | | | | | -32.5 | | | -32.5 | |

FIG. 9B

| Time | Starting Sugar | Toasts | Meal 1 | Meal 2 | Meal Total | Insulin | Dose 1 | Dose 2 | Dose 3 | Total | Ending Sugar |
|---|---|---|---|---|---|---|---|---|---|---|---|
| 4:00 pm | | 1 +54 | | | | 1 -297 | -16 | | | -16 | |
| 5:00 pm | | | | | | | -16 | | | -16 | |
| 6:00 pm | | 3 +162 | | | | | -16 | -32 | | -48 | |
| 7:00 pm | | | | | | | -16 | -32 | | -48 | |
| 8:00 pm | | | | | | | -16 | -32 | | -48 | |
| 9:00 pm | | 1 +54 | | | | | -16 | -32 | | -48 | |
| 10:00 pm | | | | | | | | -32 | | -32 | |
| 11:00 pm | | | | | | | | -32 | | -32 | |

FIG. 9C

| Time | Starting Sugar | Toasts | Meal 1 | Meal 2 | Meal Total | Insulin | Dose 1 | Dose 2 | Dose 3 | Total | Ending Sugar |
|---|---|---|---|---|---|---|---|---|---|---|---|
| 12:00 am | | | | | | | | | | | |
| 1:00 am | | | | | | | ↵16 | ↵16 | | ↵16 | |
| 2:00 am | | | | | | | ↵16 | ↵16 | | ↵16 | |
| 3:00 am | | | | | | | ↵16 | ↵16 | | ↵16 | |
| 4:00 am | | | | | | | ↵16 | ↵16 | | ↵16 | |
| 5:00 am | | | | | | | ↵16 | ↵16 | | ↵16 | |
| 6:00 am | | | | | | | ↵16 | ↵16 | | ↵16 | |
| 7:00 am | | | | | | | | | | | |

FIG.10A

| Time | Starting Sugar | Toasts | 1 | 2 | Total | Insulin | 1 | 2 | 3 | Total | Ending Sugar |
|---|---|---|---|---|---|---|---|---|---|---|---|
| 8:00 am | 108 | 1 +54 | +18 | | +18 | 11 -297 | -32.5 | | | -32.5 | 126 |
| 9:00 am | 126 | | +18 | | +18 | | -32.5 | | | -32.5 | 144 |
| 10:00 am | 144 | 1 +54 | +18 | +18 | +36 | | -32.5 | | | -32.5 | 148 |
| 11:00 am | 148 | | | +18 | +18 | | -32.5 | | | -32.5 | 133 |
| 12:00 pm | 133 | 3 +162 | +54 | +18 | +72 | | -32.5 | | | -32.5 | 173 |
| 1:00 pm | 173 | | +54 | | +54 | | -32.5 | | | -32.5 | 195 |
| 2:00 pm | 195 | 1 +54 | +54 | +18 | +72 | | -32.5 | | | -32.5 | 234 |
| 3:00 pm | 234 | | | +18 | +18 | | -32.5 | | | -32.5 | 220 |

FIG. 10B

| Time | Starting Sugar | Toasts | Meal 1 | Meal 2 | Total | Insulin | Dose 1 | Dose 2 | Dose 3 | Total | Ending Sugar |
|---|---|---|---|---|---|---|---|---|---|---|---|
| 4:00 pm | 220 | | | | | | | | | | |
| 5:00 pm | 240 | 1 +54 | +18 | +18 | +36 | 1 -297 | -16 | | | -16 | 240 |
| 6:00 pm | 242 | | +18 | | +18 | | -16 | | | -16 | 242 |
| 7:00 pm | 266 | 3 +162 | +18 | +54 | +72 | | -16 | -32 | | -48 | 266 |
| 8:00 pm | 272 | | | +54 | +54 | | -16 | -32 | | -48 | 272 |
| 9:00 pm | 278 | 3 +54 | | +54 | +54 | | -16 | -32 | | -48 | 278 |
| 10:00 pm | 248 | | +18 | | +18 | | -16 | -32 | | -48 | 248 |
| 11:00 pm | 234 | | +18 | | +18 | | | -32 | | -32 | 234 |
| | | | +18 | | +18 | | | -32 | | -32 | 220 |

FIG. 10C

| Time | Starting Sugar | Toasts | | | Total | Insulin | | | Total | Ending Sugar |
|---|---|---|---|---|---|---|---|---|---|---|
| | | | 1 | 2 | | 1 | 2 | 3 | | |
| 12:00 am | 220 | | | | | | -16 | | -16 | 204 |
| 1:00 am | 204 | | | | | | -16 | | -16 | 188 |
| 2:00 am | 188 | | | | | | -16 | | -16 | 172 |
| 3:00 am | 172 | | | | | | -16 | | -15 | 156 |
| 4:00 am | 156 | | | | | | -16 | | -16 | 140 |
| 5:00 am | 140 | | | | | | -16 | | -16 | 124 |
| 6:00 am | 124 | | | | | | | | | 124 |
| 7:00 am | 124 | | | | | | | | | 124 |

FIG. 11A

| Time | Starting Sugar | Toasts | 1 | 2 | Total | Insulin | 1 | 2 | 3 | Total | Ending Sugar |
|---|---|---|---|---|---|---|---|---|---|---|---|
| 8:00 am | 108 | 1 +54 | | | | | | | | | |
| 9:00 am | 126 | | +18 | | +18 | 1 -297 | | | | | 126 |
| 10:00 am | 144 | 1 +54 | +18 | +18 | +36 | | | | | | 144 |
| 11:00 am | 147.5 | | | +18 | +18 | | -32.5 | | | -32.5 | 147.5 |
| 12:00 pm | 133 | 3 +162 | +54 | +18 | +72 | | -32.5 | | | -32.5 | 133 |
| 1:00 pm | 172.5 | | +54 | | +54 | | -32.5 | | | -32.5 | 172.5 |
| 2:00 pm | 194 | 1 +54 | +54 | +18 | +72 | | -32.5 | | | -32.5 | 194 |
| 3:00 pm | 233.5 | | | +18 | +18 | | -32.5 | | | -32.5 | 219 |

FIG. 11B

| Time | Starting Sugar | Toasts | 1 | 2 | Total | Insulin | 1 | 2 | 3 | Total | Ending Sugar |
|---|---|---|---|---|---|---|---|---|---|---|---|
| 4:00 pm | 219 | 1 +54 | | +18+18 | +36 | | | | | | |
| 5:00 pm | 239 | | +18 | | +18 | | -16.2 | | | -16.2 | 239 |
| 6:00 pm | 240.5 | 3 +162 | +18 | +54 | +72 | 1 -297 | -16.2 | | | -16.2 | 240.5 |
| 7:00 pm | 296.5 | | | +54 | +54 | | -16.2 | | | -16.2 | 296.5 |
| 8:00 pm | 334 | 1 +54 | | +54 | +54 | | -16.2 | | | -16.2 | 334 |
| 9:00 pm | 339.5 | | +18 | | +18 | | -16.2 | -32.4 | | -48.6 | 339.5 |
| 10:00 pm | 309 | | +18 | | +18 | | -16.2 | -32.4 | | -48.6 | 309 |
| 11:00 pm | 294.5 | | +18 | | +18 | | | -32.4 | | -32.4 | 294.5 |
| | | | | | | | | -32.4 | | -32.4 | 280 |

FIG. 11C

| Time | Starting Sugar | Toasts | Meal | | Total | Insulin | Dose | | | Total | Ending Sugar |
|---|---|---|---|---|---|---|---|---|---|---|---|
| | | | 1 | 2 | | | 1 | 2 | 3 | | |
| 12:00 am | 280 | | | | | | | -32.4 | | -32.4 | 247.5 |
| 1:00 am | 247.5 | | | | | | | -32.4 | | -32.4 | 215 |
| 2:00 am | 215 | | | | | | | -16.2 | | -16.2 | 199 |
| 3:00 am | 199 | | | | | | | -16.2 | | -16.2 | 183 |
| 4:00 am | 183 | | | | | | | -16.2 | | -16.2 | 166.5 |
| 5:00 am | 166.5 | | | | | | | -16.2 | | -16.2 | 150.5 |
| 6:00 am | 150.5 | | | | | | | -16.2 | | -16.2 | 134 |
| 7:00 am | 134 | | | | | | | -16.2 | | -16.2 | 118 |

FIG.12A

| Time | Starting Sugar | Toasts | 1 | 2 | Total | Insulin | 1 | 2 | 3 | Total | Ending Sugar |
|---|---|---|---|---|---|---|---|---|---|---|---|
| 8:00 am | 108 | 1 +54 | +18 | | +18 | 15 -405 | | | | | 126 |
| 9:00 am | 126 | | +18 | | +18 | | | | | | 144 |
| 10:00 am | 144 | 1 +54 | +18 | +18 | +36 | | -45 | | | -45 | 135 |
| 11:00 am | 135 | | | +18 | +17 | | -45 | | | -45 | 108 |
| 12:00 pm | 108 | 3 +162 | +54 | +18 | +72 | | -45 | | | -45 | 135 |
| 1:00 pm | 135 | | +54 | | +54 | | -45 | | | -45 | 144 |
| 2:00 pm | 144 | 1 +54 | +54 | +18 | +72 | | -45 | | | -45 | 171 |
| 3:00 pm | 171 | | | +18 | +18 | | -45 | | | -45 | 144 |

FIG. 12B

| Time | Starting Sugar | Toasts | 1 | 2 | Total | Insulin | 1 | 2 | 3 | Total | Ending Sugar |
|---|---|---|---|---|---|---|---|---|---|---|---|
| 4:00 pm | 144 | 1 +54 | +18 | +18 | +36 | -189 | -22.5 | | | -22.5 | 157.5 |
| 5:00 pm | 157.5 | | +18 | | +18 | | -22.5 | | | -22.5 | 153 |
| 6:00 pm | 153 | 3 +162 | +18 | +54 | +72 | | -22.5 | -21 | | -43.5 | 181.5 |
| 7:00 pm | 181.5 | | | +54 | +54 | | -22.5 | -21 | | -43.5 | 192 |
| 8:00 pm | 192 | 1 +54 | +18 | +54 | +54 | | -22.5 | -21 | | -43.5 | 202.5 |
| 9:00 pm | 202.5 | | +18 | | +18 | | -22.5 | -21 | | -43.5 | 177 |
| 10:00 pm | 177 | | +18 | | +18 | | | -21 | | -21 | 174 |
| 11:00 pm | 174 | | +18 | | +18 | | | -21 | | -21 | 171 |

FIG.12C

| Time | Starting Sugar | Toasts | | | Total | Insulin | | | Total | Ending Sugar |
|---|---|---|---|---|---|---|---|---|---|---|
| | | | 1 | 2 | | | 1 | 2 | 3 | |
| 12:00 am | 171 | | | | | | | -10.5 | | 160.5 |
| 1:00 am | 160.5 | | | | | | | -10.5 | | 150 |
| 2:00 am | 150 | | | | | | | -10.5 | | 139.5 |
| 3:00 am | 139.5 | | | | | | | -10.5 | | 129 |
| 4:00 am | 129 | | | | | | | -10.5 | | 118.5 |
| 5:00 am | 118.5 | | | | | | | -10.5 | | 108 |
| 6:00 am | 108 | | | | | | | | | 108 |
| 7:00 am | 108 | | | | | | | | | 108 |

FIG.13A

| Time | Starting Sugar | Toasts | 1 | 2 | Total | Insulin | 1 | 2 | 3 | Total | Ending Sugar |
|---|---|---|---|---|---|---|---|---|---|---|---|
| 8:00 am | 108 | 1 +54 | +18 | | +18 | | | | | | 126 |
| 9:00 am | 126 | | +18 | | +18 | | | | | | 144 |
| 10:00 am | 144 | 1 +54 | +18 | +18 | +36 | | -54 | | | -54 | 126 |
| 11:00 am | 126 | | | +18 | +18 | | -54 | | | -54 | 90 |
| 12:00 pm | 90 | 3 +162 | +54 | +18 | +72 | 18 -486 | -54 | | | -54 | 108 |
| 1:00 pm | 108 | | +54 | | +54 | | -54 | | | -54 | 108 |
| 2:00 pm | 108 | 1 +54 | +54 | +18 | +72 | | -54 | | | -54 | 126 |
| 3:00 pm | 126 | | | +18 | +18 | | -54 | | | -54 | 90 |

FIG. 13B

| Time | Starting Sugar | Toasts | | 1 | 2 | Total | Insulin | | 1 | 2 | 3 | Total | Ending Sugar |
|---|---|---|---|---|---|---|---|---|---|---|---|---|---|
| 4:00 pm | 90 | 1 +54 | | +18 | +18 | +36 | 4 -108 | | -27 | | | -27 | 99 |
| 5:00 pm | 99 | | | +18 | | +18 | | | -27 | | | -27 | 90 |
| 6:00 pm | 90 | 3 +162 | | +18 | +54 | +72 | | | -27 | -13 | | -40 | 122 |
| 7:00 pm | 122 | | | | +54 | +54 | | | -27 | -13 | | -40 | 136 |
| 8:00 pm | 136 | | | | +54 | +54 | | | -27 | -13 | | -40 | 150 |
| 9:00 pm | 150 | | | | | | | | -27 | -13 | | -40 | 110 |
| 10:00 pm | 110 | 1 +54 | | +18 | | +18 | | | | -13 | | -13 | 115 |
| 11:00 pm | 115 | | | +18 | | +18 | | | | -13 | | -13 | 120 |

FIG.14

| Time | Starting Sugar | Toasts | 1 | 2 | Total | Insulin | 1 | 2 | 3 | Total | Ending Sugar |
|---|---|---|---|---|---|---|---|---|---|---|---|
| 8:00 am | 144 | | | | | | | | | | 144 |
| 9:00 am | 144 | | | | | 18 -486 | | | | | 144 |
| 10:00 am | 144 | 2 +108 | +36 | | +36 | | -54 | | | -54 | 126 |
| 11:00 am | 126 | | +36 | | +36 | | -54 | | | -54 | 108 |
| 12:00 pm | 108 | | +36 | | +36 | | -54 | | | -54 | |
| 1:00 pm | 90 | | | | | | -54 | | | -54 | |
| 2:00 pm | | | | | | | -54 | | | -54 | |
| 3:00 pm | | | | | | | -54 | | | -54 | |

FIG.15

| Time | Starting Sugar | Toasts | 1 | 2 | Total | Insulin | 1 | 2 | 3 | Total | Ending Sugar |
|---|---|---|---|---|---|---|---|---|---|---|---|
| 8:00 am | 144 | | | | | | | | | | 144 |
| 9:00 am | 144 | | | | | | | | | | 144 |
| 10:00 am | 144 | 2 +108 | +36 | | +36 | | -54 | | | -54 | 126 |
| 11:00 am | 126 | | +36 | | +36 | | -54 | | | -54 | 108 |
| 12:00 pm | 108 | | +36 | | +36 | 18 -486 | -54 | | | -54 | 90 |
| 1:00 pm | 90 | 3.5 +189 | +63 | | +63 | | -54 | | | -54 | 99 |
| 2:00 pm | 99 | | +63 | | +63 | | -54 | | | -54 | 108 |
| 3:00 pm | 108 | | +63 | | +63 | | -54 | | | -54 | 117 |

FIG. 15 b

| Time | Starting Sugar | Toasts | | | Total | Insulin | | | | Total | Ending Sugar |
|---|---|---|---|---|---|---|---|---|---|---|---|
| | | | 1 | 2 | | | 1 | 2 | 3 | | |
| 4:00 pm | 117 | | | | | 4 -108 | -27 | | | -27 | 90 |
| 5:00 pm | 90 | 3 +162 | +54 | +54 | +54 | | -27 | | | -27 | 117 |
| 6:00 pm | 117 | | +54 | +54 | +54 | | -27 | -12 | | -39 | 132 |
| 7:00 pm | 132 | | +54 | +54 | +54 | | -27 | -12 | | -39 | 147 |
| 8:00 pm | 147 | 1 +54 | +18 | +18 | +18 | | -27 | -12 | | -39 | 126 |
| 9:00 pm | 126 | | +18 | +18 | +18 | | -27 | -12 | | -39 | 105 |
| 10:00 pm | 105 | 1 +54 | +18 +18 | | +36 | | | -12 | | -12 | 129 |
| 11:00 pm | 129 | | +18 | | +18 | | | -12 | | -12 | 135 |

FIG.15 c

| Time | Starting Sugar | Toasts | | | | Insulin | | | | Ending Sugar |
|---|---|---|---|---|---|---|---|---|---|---|
| | | 1 | 2 | Total | | 1 | 2 | 3 | Total | |
| 12:00 am | ↓135 | | | | | | | | | |
| 1:00 am | ↑147 | +↑18 | | +↑18 | | | ↓6 | | ↓6 | ↓147 |
| 2:00 am | ↑141 | | | | | | ↓6 | | ↓6 | ↓141 |
| 3:00 am | ↓135 | | | | | | ↓6 | | ↓6 | ↓135 |
| 4:00 am | ↓129 | | | | | | ↓6 | | ↓6 | ↓129 |
| 5:00 am | ↓123 | | | | | | ↓6 | | ↓6 | ↓123 |
| 6:00 am | ↓117 | | | | | | | | | ↓117 |
| 7:00 am | ↓117 | | | | | | | | | ↓117 |

FIG.16

| Time | Starting Sugar | Toasts | 1 | 2 | Total | Insulin | 1 | 2 | 3 | Total | Ending Sugar |
|---|---|---|---|---|---|---|---|---|---|---|---|
| 8:00 am | 144 | | | | | | | | | | 144 |
| 9:00 am | 144 | | | | | 18 -486 | | | | | 144 |
| 10:00 am | 144 | 2 +108 | +36 | | +36 | | -54 | | | -54 | 126 |
| 11:00 am | 126 | | +36 | | +36 | | -54 | | | -54 | 108 |
| 12:00 pm | 108 | 2.5 +135 | +36 | +45 | +81 | | -54 | | | -54 | 135 |
| 1:00 pm | 135 | | | +45 | +45 | | -54 | | | -54 | 126 |
| 2:00 pm | 126 | | | +45 | +45 | | -54 | | | -54 | 117 |
| 3:00 pm | 117 | 1 +54 | +54 | | +54 | | -54 | | | -54 | 117 |

FIG. 17A

| Time | Starting Sugar | Toasts | 1 | 2 | Total | Insulin | 1 | 2 | 3 | Total | Ending Sugar |
|---|---|---|---|---|---|---|---|---|---|---|---|
| 8:00 am | 108 | 1 +54 | | | | | | | | | |
| 9:00 am | 126 | | +18 | | +18 | | | | | | 126 |
| 10:00 am | 144 | 1 +54 | +18 | | +18 | 18 -486 | | | | | 144 |
| 11:00 am | 126 | | +18 | +18 | +36 | | -54 | | | -54 | 126 |
| 12:00 pm | 90 | 5 +270 | | +18 | +18 | 4 -108 | -54 | | | -54 | 90 |
| 1:00 pm | 131 | | +90 | +18 | +108 | | -54 | -13 | | -67 | 131 |
| 2:00 pm | 154 | | +90 | | +90 | | -54 | -13 | | -67 | 154 |
| 3:00 pm | 177 | | +90 | | +90 | | -54 | -13 | | -67 | 177 |
| | | | | | | | -54 | -13 | | -67 | 110 |

FIG. 17B

| Time | Starting Sugar | Toasts | | Total | Insulin | | | Total | Ending Sugar |
|---|---|---|---|---|---|---|---|---|---|
| | | | 1 | 2 | | 1 | 2 | 3 | |
| 4:00 pm | 110 | 2 +108 | +36 | | +36 | 6 -162 | -27 | -13 | | -40 | 106 |
| 5:00 pm | 106 | | +36 | | +36 | | -27 | -13 | | -40 | 102 |
| 6:00 pm | 102 | | +36 | | +36 | | -27 | -5 | -18 | -50 | 88 |
| 7:00 pm | 88 | 3 +162 | +54 | | +54 | | -27 | -5 | -18 | -50 | 92 |
| 8:00 pm | 92 | | +54 | | +54 | | -27 | -5 | -18 | -50 | 96 |
| 9:00 pm | 96 | | +54 | | +54 | | -27 | -5 | -18 | -50 | 100 |
| 10:00 pm | 100 | 2 +108 | +36 | | +36 | | | -5 | -18 | -23 | 113 |
| 11:00 pm | 113 | | +36 | | +36 | | | -5 | -18 | -23 | 126 |

FIG. 17C

| Time | Starting Sugar | Toasts | | | | Insulin | | | | Ending Sugar |
|---|---|---|---|---|---|---|---|---|---|---|
| | | 1 | 2 | Total | | 1 | 2 | 3 | Total | |
| 12:00 am | 126 | +36 | | +36 | | | | | | 153 |
| 1:00 am | 153 | | | | | | | -9 | -9 | 144 |
| 2:00 am | 144 | | | | | | | -9 | -9 | 135 |
| 3:00 am | 135 | | | | | | | -9 | -9 | 126 |
| 4:00 am | 126 | | | | | | | -9 | -9 | 117 |
| 5:00 am | 117 | | | | | | | -9 | -9 | 108 |
| 6:00 am | 108 | | | | | | | | | 108 |
| 7:00 am | 108 | | | | | | | | | 108 |

| Time | Starting Sugar | Toasts | 1 | 2 | Total | Insulin | 1 | 2 | 3 | Total | Ending Sugar |
|---|---|---|---|---|---|---|---|---|---|---|---|
| 8:00 am | 108 | 1 +54 | | | | | | | | | |
| 9:00 am | 126 | | +18 | | +18 | 18 -486 | | | | | 126 |
| 10:00 am | 144 | 1 +54 | +18 | +18 | +36 | | | | | | 144 |
| 11:00 am | 126 | | | +18 | +18 | 4 -108 | -54 | | | -54 | 126 |
| 12:00 pm | 90 | 5 +270 | +90 | +18 | +108 | | -54 | | | -54 | 90 |
| 1:00 pm | 131 | | +90 | | +90 | | -54 | -13 | | -67 | 131 |
| 2:00 pm | 154 | | +90 | | +90 | | -54 | -13 | | -67 | 154 |
| 3:00 pm | 177 | | | | | | -54 | -13 | | -67 | 110 |

FIG. 18A

FIG. 18B

| Time | Starting Sugar | Toasts | | | | Insulin | | | | Ending Sugar |
|---|---|---|---|---|---|---|---|---|---|---|
| | | | 1 | 2 | Total | | 1 | 2 | 3 | Total |
| 4:00 pm | 110 | 2 +108 | +36 | | +36 | | -27 | -13 | | -40 | 106 |
| 5:00 pm | 106 | | +36 | | +36 | | -27 | -13 | | -40 | 102 |
| 6:00 pm | 102 | 1 +54 | +36 | +18 | +54 | | -27 | -5 | | -32 | 124 |
| 7:00 pm | 124 | | | +18 | +18 | | -27 | -5 | | -32 | 110 |
| 8:00 pm | 110 | | | +18 | +18 | | -27 | -5 | | -32 | 96 |
| 9:00 pm | 96 | 1 +54 | +18 | | +18 | | -27 | -5 | | -32 | 82 |
| 10:00 pm | 82 | | +18 | | +18 | | | -5 | | -5 | 95 |
| 11:00 pm | 95 | | +18 | | +18 | | | -5 | | -5 | 108 |

FIG. 18C

| Time | Starting Sugar | Toasts | | | | Insulin | | | | Ending Sugar |
|------|----------------|--------|---|---|-------|---------|---|---|-------|--------------|
|      |                | 1 | 2 | Total | | 1 | 2 | 3 | Total |              |
| 12:00 am | 108 | | | | | | | | | 108 |
| 1:00 am  | 108 | | | | | | | | | 108 |
| 2:00 am  | 108 | | | | | | | | | 108 |
| 3:00 am  | 108 | | | | | | | | | 108 |
| 4:00 am  | 108 | | | | | | | | | 108 |
| 5:00 am  | 108 | | | | | | | | | 108 |
| 6:00 am  | 108 | | | | | | | | | 108 |
| 7:00 am  | 108 | | | | | | | | | 108 |

FIG. 19A

| Time | Starting Sugar | Toasts | 1 | 2 | Total | Insulin | 1 | 2 | 3 | Total | Ending Sugar |
|---|---|---|---|---|---|---|---|---|---|---|---|
| 8:00 am | 108 | 1 +54 | +18 | | +18 | 18 -486 | | | | | 126 |
| 9:00 am | 126 | | +18 | | +18 | | | | | | 144 |
| 10:00 am | 144 | 1 +54 | +18 | +18 | +36 | | -54 | | | -54 | 126 |
| 11:00 am | 126 | 3 +162 | | +18 | +18 | | -54 | | | -54 | 90 |
| 12:00 pm | 90 | | +54 | +18 | +72 | | -54 | | | -54 | 108 |
| 1:00 pm | 108 | | +54 | | +54 | | -54 | | | -54 | 108 |
| 2:00 pm | 108 | 1 +54 | +54 | +18 | +72 | | -54 | | | -54 | 126 |
| 3:00 pm | 126 | | | +18 | +18 | | -54 | | | -54 | 90 |

FIG. 19B

| Time | Starting Sugar | Toasts | | 1 | 2 | Total | Insulin | 1 | 2 | 3 | Total | Ending Sugar |
|---|---|---|---|---|---|---|---|---|---|---|---|---|
| 4:00 pm | 90 | | | | | | | | | | | |
| 5:00 pm | 99 | 1 +54 | | +18 | +18 | +36 | | -27 | | | -27 | 99 |
| 6:00 pm | 90 | | | +18 | | +18 | | -27 | | | -27 | 90 |
| 7:00 pm | 141 | 5 +270 | | +18 | +90 | +108 | 10 -270 | -27 | -30 | | -57 | 141 |
| 8:00 pm | 174 | | | | +90 | +90 | | -27 | -30 | | -57 | 174 |
| 9:00 pm | 207 | | | | +90 | +90 | | -27 | -30 | | -57 | 207 |
| 10:00 pm | 150 | 1 +54 | | +18 | | +18 | | -27 | -30 | | -57 | 150 |
| 11:00 pm | 138 | | | +18 | | +18 | | | -30 | | -30 | 138 |
| | | | | | | | | | -30 | | -30 | 126 |

FIG. 19C

| Time | Starting Sugar | Toasts | Insulin | | | | | | Ending Sugar |
|---|---|---|---|---|---|---|---|---|---|
| | | | 1 | 2 | Total | 1 | 2 | 3 | Total | |
| 12:00 am | 126 | 1 +54 | +18 | +18 | +36 | | | | | 147 |
| 1:00 am | 147 | | | +18 | +18 | | -15 | | -15 | 150 |
| 2:00 am | 150 | | | +18 | +18 | | -15 | | -15 | 153 |
| 3:00 am | 153 | | | | | | -15 | | -15 | 138 |
| 4:00 am | 138 | | | | | | -15 | | -15 | 123 |
| 5:00 am | 123 | | | | | | -15 | | -15 | 108 |
| 6:00 am | 108 | | | | | | | | | 108 |
| 7:00 am | 108 | | | | | | | | | 108 |

FIG. 20A

| Time | Starting Sugar | Toasts | 1 | 2 | Total | Insulin | 1 | 2 | 3 | Total | Ending Sugar |
|---|---|---|---|---|---|---|---|---|---|---|---|
| 9:00 am | 108 | 2 +108 | | | | 12 -108 | | | | | 108 |
| 10:00 am | 108 | | +36 | | +36 | | -36 | | | -36 | 144 |
| 11:00 am | 144 | | +36 | | +36 | | -36 | | | -36 | 144 |
| 12:00 pm | 144 | | +36 | | +36 | | -36 | | | -36 | 144 |
| 1:00 pm | 144 | 3 +162 | +54 | | +54 | 18 -162 | -54 | | | -54 | 108 |
| 2:00 pm | 108 | | +54 | | +54 | | -54 | | | -54 | 108 |
| 3:00 pm | 108 | 1 +54 | +54 | +18 | +72 | 6 -162 | -54 | | | -54 | 126 |
| 4:00 pm | 126 | | | +18 | +18 | | -18 | | | -18 | 126 |

FIG. 20B

| Time | Starting Sugar | Toasts | | | Insulin | | | | Ending Sugar |
|---|---|---|---|---|---|---|---|---|---|
| | | | 1 | 2 | Total | | 1 | 2 | 3 | Total | |
| 5:00 pm | 126 | | | +18 | +18 | | -18 | | | -18 | 126 |
| 6:00 pm | 126 | 3 +1.62 | | | | 13 -1.62 | -18 | | | -18 | 108 |
| 7:00 pm | 108 | | +54 | | +54 | | -54 | | | -54 | 108 |
| 8:00 pm | 108 | | +54 | | +54 | | -54 | | | -54 | 108 |
| 9:00 pm | 108 | | +54 | | +54 | 6 -54 | -54 | | | -54 | 108 |
| 10:00 pm | 108 | 1 +54 | +18 | | +18 | | -18 | | | -18 | 108 |

FIG. 21A

| | Time | | Sample Results |
|---|---|---|---|
| Step 1 | Time = 8:00 am | Blood sugar reading | 180 |
| Step 2 | Immediately = 8:00 am | Eat 2 Toasts | |
| Step 3 | +1/2 hour, Time = 8:30 am | Blood sugar reading | 198 |
| | +1/2 hour, Time = 9:00 am | Blood sugar reading | 215 |
| | +1/2 hour, Time = 9:30 am | Blood sugar reading | 234 |
| | +1/2 hour, Time =10:00 am | Blood sugar reading | 250 |
| | +1/2 hour, Time = 10:30 am | Blood sugar reading | 270 |
| | +1/2 hour, Time = 11:00 am | Blood sugar reading | 288 |

| | Time | | Your Results |
|---|---|---|---|
| Step 4 | Immediately 11:00 am | Take 12 units of fast-acting insulin | |
| Step 5 | +1/2 hour, Time = 11:30 am | Blood sugar reading | 270 |
| | +1/2 hour, Time = 12:00 pm | Blood sugar reading | 250 |
| | +1/2 hour, Time = 12:30 pm | Blood sugar reading | 234 |
| | +1/2 hour, Time = 1:00 pm | Blood sugar reading | 215 |
| | +1/2 hour, Time = 1:30 pm | Blood sugar reading | 198 |
| | +1/2 hour, Time = 2:00 pm | Blood sugar reading | 180 |

FIG. 21B

FIG. 22

|  | Time | | Original Results | Exercise Results |
|---|---|---|---|---|
| Step 1 | Starting Time 8:00 am | Starting Blood sugar reading | 180 | 144 |
| Step 2 | Immediately 8:00 am | Eat 2 toasts | | |
| Step 3 | 1/2 hour later 8:30 am | Your typical exercise | | |
|  |  | Normal morning activities | | |
|  | 3 hrs after first reading 11:00 am | Blood sugar reading | 288 | 198 |

FIG.23A

| Time | Starting Sugar | Toasts | | 1 | 2 | Total | Insulin | | 1 | 2 | 3 | Total | Ending Sugar |
|---|---|---|---|---|---|---|---|---|---|---|---|---|---|
| 8:00 am | 108 | | | | | | | | | | | | 108 |
| 9:00 am | 108 | 2 | +108 | +36 | +36 | +36 | 12 | -108 | -36 | | | -36 | 108 |
| 10:00 am | 108 | | | +36 | +36 | +36 | | | -36 | | | -36 | 108 |
| 11:00 am | 108 | | | +36 | +36 | +36 | | | -36 | | | -36 | 108 |
| 12:00 pm | 108 | | | | | | | | | | | | 108 |
| 1:00 pm | 108 | 3 | +162 | +54 | +54 | +54 | 18 | -162 | -54 | | | -54 | 108 |
| 2:00 pm | 108 | | | +54 | +54 | +54 | | | -54 | | | -54 | 108 |
| 3:00 pm | 108 | 1 | +54 | +54 | +18 | +72 | 6 | -54 | -54 | -18 | | -72 | 108 |

FIG. 23B

| Time | Starting Sugar | Toasts | 1 | 2 | Total | Insulin | 1 | 2 | 3 | Total | Ending Sugar |
|---|---|---|---|---|---|---|---|---|---|---|---|
| 4:00 pm | 108 | | | +18 | +18 | | | -18 | | -18 | 108 |
| 5:00 pm | 108 | | | +18 | +18 | | | -18 | | -18 | 108 |
| 6:00 pm | 108 | 3, +162 | | | | 18, -162 | -54 | | | -54 | 54 |
| 7:00 pm | 54 | | +54 | | +54 | | -54 | | | -54 | 54 |
| 8:00 pm | 54 | | +54 | | +54 | | -54 | | | -54 | 54 |
| 9:00 pm | 54 | | -54 | | -54 | 6, -54 | -18 | | | -18 | 90 |
| 10:00 pm | 90 | | +18 | | +18 | | -18 | | | -18 | 90 |
| 11:00 pm | 90 | 1, +54 | +18 | | +18 | 26(i) | -18 | | | -18 | 90 |

FIG. 23C

| Time | Starting Sugar | Toasts 1 | 2 | Total | Insulin 1 | 2 | 3 | Total | Ending Sugar |
|---|---|---|---|---|---|---|---|---|---|
| 12:00 am | 90 | +↑8 | | +↑8 | | | | | 108 |
| 1:00 am | 108 | | | | | | | | 108 |
| 2:00 am | 108 | | | | | | | | 108 |
| 3:00 am | 108 | | | | | | | | 108 |
| 4:00 am | 108 | | | | | | | | 108 |
| 5:00 am | 108 | | | | | | | | 108 |
| 6:00 am | 108 | | | | | | | | 108 |
| 7:00 am | 108 | | | | | | | | 108 |

FIG.24A

| Time | Starting Sugar | Toasts | 1 | 2 | Total | Insulin | 1 | 2 | 3 | Total | Ending Sugar |
|---|---|---|---|---|---|---|---|---|---|---|---|
| 8:00 am | 108 | | | | | | | | | | 108 |
| 9:00 am | 108 | 2 +108 | +36 | | +36 | | | | | | 144 |
| 10:00 am | 144 | | +36 | | +36 | 12 -108 | -36 | | | -36 | 144 |
| 11:00 am | 144 | | +36 | | +36 | | -36 | | | -36 | 144 |
| 12:00 pm | 144 | | | | | | -36 | | | -36 | 108 |
| 1:00 pm | 108 | 3 +162 | +54 | | +54 | 18 -162 | | | | | 162 |
| 2:00 pm | 162 | | +54 | | +54 | | -54 | | | -54 | 162 |
| 3:00 pm | 162 | 1 +54 | +54 | +18 | +72 | 6 -54 | -54 | | | -54 | 180 |

| Time | Starting Sugar | Toasts | 1 | 2 | Total | Insulin | 1 | 2 | 3 | Total | Ending Sugar |
|---|---|---|---|---|---|---|---|---|---|---|---|
| 4:00 pm | 180 | | | | | | -54 | -18 | | -72 | 126 |
| 5:00 pm | 126 | | | +18 | +18 | | | -18 | | -18 | 108 |
| 6:00 pm | 126 | 3 +162 | | +18 | +18 | 18 -162 | | -18 | | -18 | 108 |
| 7:00 pm | 108 | | +54 | | +54 | | -54 | | | -54 | 108 |
| 8:00 pm | 108 | | +54 | | +54 | | -54 | | | -54 | 108 |
| 9:00 pm | 108 | 1 +54 | +54 | | +54 | 6 -54 | -54 | | | -54 | 108 |
| 10:00 pm | 108 | | +18 | | +18 | | -18 | | | -18 | 108 |
| 11:00 pm | 108 | | +18 | | +18 | 26 (i) | -18 | | | -18 | 108 |

FIG. 24B

FIG. 24C

| Time | Starting Sugar | Toasts | | | Insulin | | | | Ending Sugar |
|---|---|---|---|---|---|---|---|---|---|
| | | 1 | 2 | Total | 1 | 2 | 3 | Total | |
| 12:00 am | 108 | | +18 | +18 | -18 | | | -18 | 108 |
| 1:00 am | 108 | | | | | | | | 108 |
| 2:00 am | 108 | | | | | | | | 108 |
| 3:00 am | 108 | | | | | | | | 108 |
| 4:00 am | 108 | | | | | | | | 108 |
| 5:00 am | 108 | | | | | | | | 108 |
| 6:00 am | 108 | | | | | | | | 108 |
| 7:00 am | 108 | | | | | | | | 108 |

FIG.25A

| Time | Starting Sugar | Toasts | 1 | 2 | Total | Insulin | 1 | 2 | 3 | Total | Ending Sugar |
|---|---|---|---|---|---|---|---|---|---|---|---|
| 8:00 am | 108 | | | | | | | | | | 108 |
| 9:00 am | 108 | 2 +108 | | | | | | | | | 108 |
| 10:00 am | 108 | | +36 | +36 | +36 | | -36 | | | -36 | 144 |
| 11:00 am | 144 | | +36 | +36 | +36 | | -36 | | | -36 | 144 |
| 12:00 pm | 144 | 3 +162 | | | | 18 -162 | -36 | | | -36 | 144 |
| 1:00 pm | 144 | | +54 | +54 | +54 | | -54 | | | -54 | 108 |
| 2:00 pm | 108 | | +54 | +54 | +54 | | -54 | | | -54 | 108 |
| 3:00 pm | 108 | 1 +54 | +54 | +54+18 | +72 | 6 -162 | -54 | | | -54 | 126 |

FIG. 25B

| Time | Starting Sugar | Toasts | 1 | 2 | Total | Insulin | 1 | 2 | 3 | Total | Ending Sugar |
|------|----------------|--------|-----|-----|-------|---------|-----|-----|-----|-------|--------------|
| 4:00 pm | 126 | | | +18 | +18 | | -18 | | | -18 | 126 |
| 5:00 pm | 126 | | | +18 | +18 | | -18 | | | -18 | 126 |
| 6:00 pm | 126 | | | | | 18 -162 | -18 | | | -18 | 108 |
| 7:00 pm | 108 | 3 +162 | +54 | | +54 | | -54 | | | -54 | 108 |
| 8:00 pm | 108 | | +54 | | +54 | | -54 | | | -54 | 108 |
| 9:00 pm | 108 | | -54 | | -54 | 6 -54 | -54 | | | -54 | 108 |
| 10:00 pm | 108 | 1 +54 | +18 | | +18 | | -18 | | | -18 | 108 |
| 11:00 pm | 108 | | +18 | | +18 | 26 (i) | -18 | | | -18 | 108 |

FIG. 25C

| Time | Starting Sugar | Toasts | | | | Insulin | | | | Ending Sugar |
|---|---|---|---|---|---|---|---|---|---|---|
| | | 1 | 2 | Total | | 1 | 2 | 3 | Total | |
| 12:00 am | 108 | +18 | | +18 | | -18 | | | -18 | 108 |
| 1:00 am | 108 | | | | | | | | | 108 |
| 2:00 am | 108 | | | | | | | | | 108 |
| 3:00 am | 108 | | | | | | | | | 108 |
| 4:00 am | 108 | | | | | | | | | 108 |
| 5:00 am | 108 | | | | | | | | | 108 |
| 6:00 am | 108 | | | | | | | | | 108 |
| 7:00 am | 108 | | | | | | | | | 108 |

FIG.26A

| Time | Starting Sugar | Toasts | | | Total | Insulin | | | | Total | Ending Sugar |
|---|---|---|---|---|---|---|---|---|---|---|---|
| | | | 1 | 2 | | | 1 | 2 | 3 | | |
| 8:00 am | 108 | | | | | | | | | | 108 |
| 9:00 am | 108 | 2 +108 | +36 | | +36 | 12 -108 | -36 | | | -36 | 108 |
| 10:00 am | 108 | | +36 | | +36 | | -36 | | | -36 | 108 |
| 11:00 am | 108 | | +36 | | +36 | | -36 | | | -36 | 108 |
| 12:00 pm | 108 | | | | | | | | | | 108 |
| 1:00 pm | 108 | 3 +162 | +54 | | +54 | 18 -162 | -54 | | | -54 | 108 |
| 2:00 pm | 108 | | +54 | | +54 | | -54 | | | -54 | 108 |
| 3:00 pm | 108 | 1 +54 | +54 | +18 | +72 | 6 -54 | -54 | -18 | | -72 | 108 |

FIG. 26B

| Time | Starting Sugar | Toasts | | | | Insulin | | | | Ending Sugar |
|------|---------------|--------|---|---|---|---------|---|---|---|--------------|
| | | | 1 | 2 | Total | | 1 | 2 | 3 | Total | |
| 4:00 pm | 108 | | | +18 | +18 | | -18 | | | -18 | 108 |
| 5:00 pm | 108 | | | +18 | +18 | | | -18 | | -18 | 108 |
| 6:00 pm | 108 | | | | | | | | | | 108 |
| 7:00 pm | 108 | 3 +162 | +54 | | +54 | 18 -162 | -54 | | | -54 | 108 |
| 8:00 pm | 108 | | +54 | | +54 | | -54 | | | -54 | 108 |
| 9:00 pm | 108 | 1 +54 | +54 | | +54 | | -54 | | | -54 | 108 |
| 10:00 pm | 108 | | +18 | | +18 | 6 -54 | -18 | | | -18 | 108 |
| 11:00 pm | 108 | | +18 | | +18 | 26(i) | -18 | | | -18 | 108 |

FIG. 26C

| Time | Starting Sugar | Toasts | | | Insulin | | | Ending Sugar |
|---|---|---|---|---|---|---|---|---|
| | | 1 | 2 | Total | 1 | 2 | 3 | Total | |
| 12:00 am | 108 | +18 | | +18 | -18 | | | -18 | 108 |
| 1:00 am | 108 | | | | | | | | 108 |
| 2:00 am | 108 | | | | | | | | 108 |
| 3:00 am | 108 | | | | | | | | 108 |
| 4:00 am | 108 | | | | | | | | 108 |
| 5:00 am | 108 | | | | | | | | 108 |
| 6:00 am | 108 | | | | | | | | 108 |
| 7:00 am | 108 | | | | | | | | 108 |

FIG.27A

| Time | Starting Sugar | Toasts | 1 | 2 | Total | Insulin | 1 | 2 | 3 | Total | Ending Sugar |
|---|---|---|---|---|---|---|---|---|---|---|---|
| 8:00 am | 108 | 1 +54 | +18 | | +18 | | | | | | 126 |
| 9:00 am | 126 | | +18 | | +18 | | | | | | 144 |
| 10:00 am | 144 | 1 +54 | +18 | +18 | +36 | 1 -486 | -54 | | | -54 | 126 |
| 11:00 am | 126 | | | +18 | +18 | | -54 | | | -54 | 90 |
| 12:00 pm | 90 | 3 +162 | +54 | +18 | +72 | | -54 | | | -54 | 108 |
| 1:00 pm | 108 | | +54 | | +54 | | -54 | | | -54 | 108 |
| 2:00 pm | 108 | 1 +54 | +54 | +18 | +72 | | -54 | | | -54 | 126 |
| 3:00 pm | 126 | | +18 | | +18 | | -54 | | | -54 | 90 |

FIG. 27B

| Time | Starting Sugar | Toasts | 1 | 2 | Total | Insulin | 1 | 2 | 3 | Total | Ending Sugar |
|---|---|---|---|---|---|---|---|---|---|---|---|
| 4:00 pm | 90 | 1 +54 | +18 | +18 | +36 | 4 -108 | -27 | | | -27 | 99 |
| 5:00 pm | 99 | | +18 | | +18 | | -27 | | | -27 | 90 |
| 6:00 pm | 90 | 3 +162 | +18 | +54 | +72 | | -27 | -12 | | -39 | 123 |
| 7:00 pm | 123 | | | +54 | +54 | | -27 | -12 | | -39 | 138 |
| 8:00 pm | 138 | | | +54 | +54 | | -27 | -12 | | -39 | 153 |
| 9:00 pm | 153 | | | | | | -27 | -12 | | -39 | 114 |
| 10:00 pm | 114 | 1 +54 | +18 | | +18 | | | -12 | | -12 | 120 |
| 11:00 pm | 120 | | +18 | | +18 | 26(i) | | -12 | | -12 | 126 |

FIG. 27C

| Time | Starting Sugar | Toasts | | | | Insulin | | | | Ending Sugar |
|---|---|---|---|---|---|---|---|---|---|---|
| | | 1 | 2 | Total | | 1 | 2 | 3 | Total | |
| 12:00 am | 126 | +18 | | +18 | | | 6 | | 6 | 138 |
| 1:00 am | 138 | | | | | | 6 | | 6 | 132 |
| 2:00 am | 132 | | | | | | 6 | | 6 | 126 |
| 3:00 am | 126 | | | | | | 6 | | 6 | 120 |
| 4:00 am | 120 | | | | | | 6 | | 6 | 114 |
| 5:00 am | 114 | | | | | | 6 | | 6 | 108 |
| 6:00 am | 108 | | | | | | | | | 108 |
| 7:00 am | 108 | | | | | | | | | 108 |

FIG.28A

Chart I

| Line | Time | | Your Results |
|---|---|---|---|
| 1 | Time = | Blood sugar reading | |
| 2 | Immediately | Eat 2 Toasts | |
| 3 | +1/2 hour, Time = | Blood sugar reading | |
| 4 | +1/2 hour, Time = | Blood sugar reading | |
| 5 | +1/2 hour, Time = | Blood sugar reading | |
| 6 | +1/2 hour, Time = | Blood sugar reading | |
| 7 | +1/2 hour, Time = | Blood sugar reading | |
| 8 | +1/2 hour, Time = | Blood sugar reading | |

Step 1
Step 2
Step 3

Chart I

| Line | Time | Your Results |
|---|---|---|
| 9 | Immediately | Take 12 units of fast-acting insulin |
| 10 | +1/2 hour, Time = | Blood sugar reading |
| 11 | +1/2 hour, Time = | Blood sugar reading |
| 12 | +1/2 hour, Time = | Blood sugar reading |
| 13 | +1/2 hour, Time = | Blood sugar reading |
| 14 | +1/2 hour, Time = | Blood sugar reading |
| 15 | +1/2 hour, Time = | Blood sugar reading |

Step 4

Step 5

FIG. 28B

FIG.29A

Chart II

| Time | Starting Sugar | Toasts | | | Total | Insulin | | | | Total | Ending Sugar |
|---|---|---|---|---|---|---|---|---|---|---|---|
| | | | 1 | 2 | | | 1 | 2 | 3 | | |
| 8:00 am | | | | | | | | | | | |
| 9:00 am | | | | | | | | | | | |
| 10:00 am | | | | | | | | | | | |
| 11:00 am | | | | | | | | | | | |
| 12:00 pm | | | | | | | | | | | |
| 1:00 pm | | | | | | | | | | | |
| 2:00 pm | | | | | | | | | | | |
| 3:00 pm | | | | | | | | | | | |

FIG. 29B

Chart II continued

FIG. 29C

Chart II continued

| Time | Starting Sugar | Toasts | 1 | 2 | Total | Insulin | 1 | 2 | 3 | Total | Ending Sugar |
|------|----------------|--------|---|---|-------|---------|---|---|---|-------|--------------|
| 12:00 am | | | | | | | | | | | |
| 1:00 am | | | | | | | | | | | |
| 2:00 am | | | | | | | | | | | |
| 3:00 am | | | | | | | | | | | |
| 4:00 am | | | | | | | | | | | |
| 5:00 am | | | | | | | | | | | |
| 6:00 am | | | | | | | | | | | |
| 7:00 am | | | | | | | | | | | |

Chart III

| Line | Time | | Original Results | Exercise Results |
|---|---|---|---|---|
| 1 | Starting Time | Starting Blood sugar reading | | |
| 2 | Immediately | Eat 2 toasts | | |
| 3 | 1/2 hour later | Your typical exercise | | |
| 4 | | Normal morning activities | | |
| 5 | 3 hrs after first reading | Blood sugar reading | | |

Step 1 → Line 1
Step 2 → Line 2
Step 3 → Line 3

FIG.30

METHOD OF FOOD AND INSULIN DOSE MANAGEMENT FOR A DIABETIC SUBJECT

CROSS-REFERENCE TO RELATED APPLICATIONS

This application claims priority from U.S. Provisional Application No. 60/498,580, filed Aug. 29, 2003; U.S. Provisional Application No. 60/420,289, filed Oct. 23, 2002; and Canadian Application No. 2,409,374, filed Oct. 23, 2002; the entire disclosures of which are incorporated herein by reference.

FIELD OF THE INVENTION

The invention relates to methods of food and insulin dosing in a diabetic patient.

BACKGROUND OF THE INVENTION

Most foods are carbohydrates, which are converted to sugar by the digestive process. Cells absorb this sugar in order to support life. Insulin, a hormone produced by the pancreas, is key to the absorption of sugar by the cells. Without this hormone being present, the cells will not absorb the sugar, and will die. A diabetic who is dependent on insulin injections typically does not produce his or her own insulin, and therefore needs to take insulin shots to survive.

The medical community uses a scale of 0 to 540 mg/dl to represent the amount of sugar in the blood. Low blood sugar is considered to be 0–70. Normal blood sugar is considered 70–126. High blood sugar is in the range 126–200. Very high blood sugar is over 200.

Below 70 is a condition known as very low blood sugar (hypoglycemia). This is the level at which brain damage and death can occur if immediate action is not taken to correct the situation. At 200 and above is a condition known as very high blood sugar (hyperglycemia). As the sugar level approaches 540, brain damage and death can occur if immediate corrective action is not taken. At both ends of the spectrum, very high and very low, a diabetic will go into a coma.

To correct a very low blood sugar condition, it is necessary to get sugar into the blood immediately, by ingesting sugar or its equivalent: for example a high-sugar fruit juice such as orange juice. In an emergency, a glucose injection can be given. Typically, blood sugar will rise within minutes.

To correct a very high sugar condition, only insulin can help. Even quick-acting insulin still takes hours to reduce a high sugar condition. It is, therefore, easier to deal with low blood sugar than high blood sugar.

Normal blood sugar levels are between 72 and 126, with a buffer up to 200. Between 200 and over 500 is the territory of the diabetic sufferer. Long-term sugar levels in this range will cause blindness, kidney failure and nerve damage, as well as increasing the risk of heart attacks fourfold. Allowing sugar to go over 200 is dangerous because at that point excess sugar will be flushed from the blood, and out through the kidneys with urine. This level of 200 is known in medical terms as the "renal threshold" with the word "renal" meaning "kidney". In other words the sugar spills from the blood, through the kidney and into the bladder.

The 108–144 range, rather than 72–126, provides a cushion to protect from a dangerous low blood sugar condition that can occur below 72. While a diabetic would prefer to stay at 126 or under, practice will show that this is hard to achieve safely. Any damage between 126 and 144 is very small, and is preferable to sliding under 72. So a diabetic may aim for 100 or 110 to 126, but is not over-concerned at a reading between 126 and 144.

As sugar edges toward the high end, a diabetic gets sleepy and lethargic. Just a little high, and the subject feels quite normal.

Those who do not know that they are diabetic have no way of seeing their blood sugar, so they feel quite well with their sugar in the 215–250 ranges. However, with sugar at that level for several years, serious damage to the body can occur.

A diabetic can lead a healthy lifestyle, and still succumb to the complications of the disease. There are four major targets of this disease, that can be attributed directly to excess blood sugar:

Arteries and Heart

As excess sugar accumulates in the bloodstream it causes the walls of the arteries to harden. This hardening will eventually contribute to clogging of arteries, leading to an increased chance of heart attack. Diabetics with poorly controlled blood sugar levels have a four times greater risk of heart attack than non-diabetics. The risk of stroke is also significantly increased.

As excess sugar accumulates in the bloodstream it causes the walls of the arteries to harden. This hardening will eventually contribute to clogging of arteries, leading to an increased chance of heart attack. Diabetics with poorly controlled blood sugar levels have a four times greater risk of heart attack than non-diabetics. The risk of stroke is also significantly increased.

Kidneys

The level 200 on the scale is the level at which the body tries to rid itself of the excess sugar, by dumping it into the urine; this is the "renal threshold". In fact, sugar in the urine is one way of diagnosing diabetes since a person without diabetes will not show sugar in the urine. Thirst and frequent urination are symptoms of diabetes because the body is trying very hard to increase the intake of fluids, which help dispose of this excess, unwanted, dangerous sugar. The body either has increased sugar in the blood, which can lead to heart failure, or releases the sugar into the urine, which can lead to kidney failure. The kidneys, however take a lot longer to fail than does the heart, so the body chooses the route that will give it the longest time to survive.

Even at 90% failure the kidneys will still operate, and the diabetic may feel quite normal. However, every 1% drop in kidney function thereafter will have the impact of losing 10% of remaining kidney function, and serious medical consequences result. Within several months of the kidney function dropping below 10%, kidney failure will occur.

Eyes

The eyes are filled with a dense fluid. When there is excess sugar in the system, this fluid becomes denser, requiring more fluid to regain its optimum density. This extra fluid is forced into a space that has very few expansion possibilities, and results in putting pressure on the retina, leading to the condition known as glaucoma. At the same time, the arteries supplying blood to the eyes also become hardened, resulting in additional pressure at the back of the eye. Caught between these two pressures, the eyes suffer a variety of complications that damage the retina, and can eventually lead to total blindness.

Other retinal disease can also be brought on as a by-product of uncontrolled diabetes.

Feet

A lot of diabetics suffer from pain in the legs and feet, eventually losing feeling in the soles of their feet. A by-product of spilled sugar is an insoluble substance called sorbitol, which gets inside the myelin sheath (insulation). After accumulating in the myelin sheath for some time, it eventually ruptures it, causing the exposed nerve to stop functioning. The resultant loss of feeling makes walking very difficult, like walking with frozen feet, and also makes it very difficult to feel any pain or discomfort.

Another complicating factor of continuing high blood sugar is poor healing. High sugar concentration in the blood leads to poor circulation, which interferes with the natural healing process. This is one of the reasons why diabetics with poor control of their sugar have ulcers that don't heal.

Food and Blood Sugar

There are two types of diabetes, called Type 1 and Type 2. The difference between them is, that most Type 2 diabetics develop their condition in adulthood, and can control it through a combination of diet, exercise, and weight control, whereas most Type 1 diabetics often develop their condition as children, and must take insulin to stay alive.

A person who does not have diabetes controls his sugar automatically and unconsciously, without being aware that it is even happening. Sugar stays in the 72 to 126 range, and any excess sugar is quickly removed, and stored as fat, for future use. The key to this automatic regulation is insulin: a hormone produced by the pancreas.

Type I diabetics lose the ability to make this hormone, often because of an autoimmune response in which antibodies destroy the cells that make insulin. They have to rely on insulin injections to live. The amount of insulin required is based on several factors, the most important one being the amount of food that is eaten. As a result, they have to be very careful about their food intake, in order to control their blood sugar.

Type 2 diabetics lose, to varying degrees, the ability to absorb insulin into their cells, where it could enable the cells to metabolize sugar. It is rendered more severe by excess weight, and is controlled by diet, exercise, pills, and sometimes by extra insulin.

Different foods have different absorption rates. For example, a half a glass of orange juice may enter the blood within five minutes. In fact, because of its speed, it is recommended as 'quick sugar' when blood sugar falls below 72. If this juice is consumed in the form of an orange, it takes much longer for it to become blood sugar. Eating unprocessed whole grain foods, such as regular oatmeal, takes hours before it all is converted to sugar.

At one end of the spectrum are 'quick sugars' like packaged cereals, and at the other end, are 'slow sugars' such as pasta or whole grain bread. Quick sugars enter the blood in about an hour, although the presence of fiber and fat can slow this down. Slow sugars take about an hour to start entering the blood stream, and this effect can spread over about three hours, or even longer. The rate at which various carbohydrate foods enter the blood as sugar is called the glycemic index. Categories of sugars are below:

Fast-absorbing: (and demanding fast-acting insulin): high glycaemic index

Highly processed grains and potatoes including packaged cereals and instant rice and potatoes.
Less processed grains, like whole wheat bread, instant oatmeal, and non-instant rice
Maltose, glucose
Carrots, parsnips and corn
Banana, raisins, apricots, papaya and mango
Corn chips snacks and low-fat ice-cream
Moderate glycaemic index Pasta, heavy breads, all-bran cereal
Oranges and orange juice
Most peas and beans
Lactose, sucrose
Candy bars, potato chips
Fairly low glycaemic index Slow cooking oatmeal, barley, heavy rye breads
Apples, pears, grapes, peaches
Less processed peas and beans
Milk, yogurt, fat ice cream
Low glycaemic index Cherries, plums, grapefruit
Fructose
Fatty beans and nuts, such as soy beans and peanuts So, in order to keep his sugar in the 72–126, or 100–144 range, the diabetic not only has to count his sugar, but must also be familiar with the absorption rates of different foods. For instance, if the sugar reading is 108 and the diabetic drinks an 8 oz. glass of orange juice, his sugar will go up to about 250 within a few minutes. It might then take 2–3 hours for it to go back to 144. Those hours in the 'spilled sugar' condition (over 200) result in diabetic complications in the future, and the time spent between 144 and 198, while not spilling sugar, still adversely affects health. If a cup of whole grain pasta is chosen instead, it would put sugar into the blood at about the rate that insulin absorbs it. As a result, the sugar is unlikely to go above 200.

The foods that convert to sugar are starches and fruits. Proteins and fats have no direct impact on blood sugar, but they do affect it indirectly.

Without going into all of the parameters in great detail, it is clear that diabetics need to watch all elements of a diet in order to achieve normal sugar levels. There is a need for a simple method to juggle the various food parameters in order to achieve healthy blood sugar levels.

Measuring Sugar

There are two basic measurements that tell how much sugar is in the blood. One measurement is the current amount of sugar in the blood.

The meters that are purchased at drug stores come in two varieties: those that measure sugar on the scale discussed above (0–540+) and those that come with a different scale (0–30$^+$), or 1/18th the 0–540 scale. The diagram below shows how these two scales correspond:

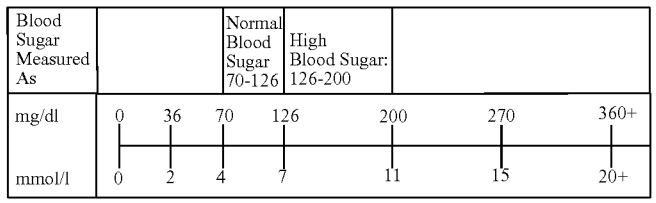

The 0–540 scale is used in the United States, and the 0–30 scale in Canada. The rest of the world uses one or the other.

It is vital that the meter be very accurate. Studies have shown, that relatively small differences in a diabetic's long-term sugar level have a significant impact on his health. 108–126 is good, while 144–162 is somewhat harmful, and over that is more seriously damaging.

The long-term blood sugar level has to be measured in a laboratory and is known as $HbA_1C$ or glycosolated hemoglobin. It is presented on a scale of 4.5% to as high as 20%, in extremely ill persons. $HbA_1C$ is one of three types of oxygen-carrying hemoglobin found in the body, and when it contacts glucose molecules in the blood, some of them stick to it. The more glucose there is in the blood, the more that sticks to the $HbA_1C$, and this can be measured to give a percentage saturation, that translates into an average blood sugar. Because $HbA_1C$ cells live about three months, this shows the level at which the blood sugar has been, on the average, over a three month period.

particular rate of carbohydrate release in a subject or the rate of sugar removal by insulin administered to the subject. There remains a need for a more precise and simple way to balance diet and insulin intake in a diabetic subject.

SUMMARY OF THE INVENTION

The invention relates to a method of food and insulin dose management for a diabetic subject, comprising:

a) providing an intended insulin unit value or an intended carbohydrate unit value representing the amount of insulin or carbohydrate intended for intake by the subject;

b) determining the balance value of either insulin units or carbohydrate units needed to balance with the provided unit value and maintain blood sugar in the subject in a target blood sugar range.

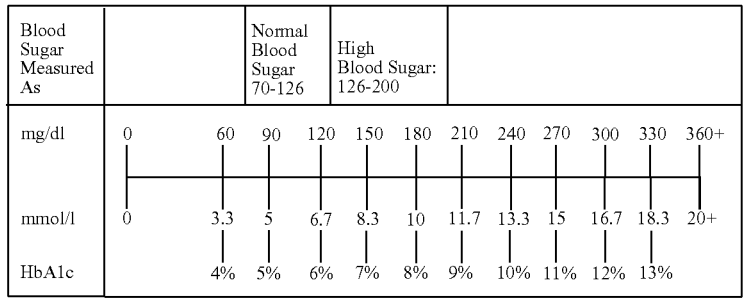

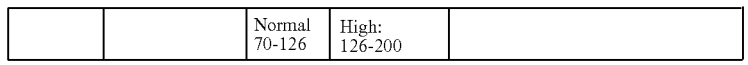

It is the three month measure that indicates how well a diabetic is controlling sugar. It is very possible to get a single high or low reading. An $HbA_1C$ reading of 6–7% indicates that a good level of control has been achieved. The current optimum $HbA_1C$ recommendation is 6.5%.

Some diabetic subjects have tried to balance carbohydrates with insulin by carbohydrate counting. This involves counting carbohydrate grams in food based on the large amount of self-management data currently available. Carbohydrate choice counting is typically based on the portion of a 15 g equivalent of carbohydrate on which the exchange system is based. The system categorizes foods by lists that have similar macronutrient and energy values. However these systems are not individualized by considering the "Insulin unit value" refers to a number of units of insulin—it can be expressed in any units that the subject uses in taking the medication.

"Balance" means to adjust insulin and carbohydrate to maintain blood sugar in a target blood sugar range. When an intended insulin value is provided by the subject, the "balance value" is the number of standard carbohydrate units or food units that the subject must take in to maintain blood sugar in a safe blood sugar range.

In one embodiment of the method, the intended carbohydrate unit value comprises an intended food unit value. "Food unit value" refers to a standard size item of food indicating an approximately known and consistent amount of carbohydrate. For example, a standard slice of toast or bread includes 16 g of carbohydrate. The balance value is preferably calculated by determining for the subject a starting blood sugar value and comparing sugar metabolism resulting from the provided unit value with sugar metabolism resulting from the insulin units or food units and thereby calculating the amount of insulin units or food units necessary to maintain blood sugar in the subject in a target blood sugar range.

Preferably, the sugar metabolism resulting from the provided unit value and sugar metabolism resulting from the insulin units or food units are determined individually for a subject from the amount of sugar and rate of release of sugar in food in the subject and the amount of sugar and rate of removal of sugar by insulin in the subject.

The method is optionally performed by or directed by the subject. In one embodiment of the invention, the subject provides an intended food unit value and the method further comprises,
 a) determining a starting blood sugar value in the subject;
 b) determining from the food unit value i) a total sugar release value and ii) a sugar release rate value;
 c) determining the balance value by determining an effective amount of insulin, insulin analog or insulin mimetic to administer to the subject to balance with the values in b) so that an ending blood sugar value in the subject is in a target blood sugar range.

"Target blood sugar range" is the range desired by the subject. It is preferably a "safe sugar range", which means 72–144, more preferably 108–144 to have a buffer to avoid a low blood sugar condition. The subject is still in a safe sugar range provided that the subject's blood sugar is not over 200–250 for more than two hours in a day and more preferably not over 150 for more than one hour in a day.

The method optionally further comprises i) the subject receiving food in accordance with the intended standard food unit value and ii) the subject receiving insulin, insulin analog or insulin mimetic containing a number of insulin units in accordance with the balance value.

In one embodiment, the subject provides an intended insulin unit value and the method further comprises,
 a) determining a starting blood sugar value in the subject;
 b) determining from the insulin unit value i) a total sugar removal value to be removed from the blood of the subject and ii) a sugar removal rate value;
 c) determining the balance value by determining an effective amount of food units to be taken in by the subject to balance with the values in b) so that an ending blood sugar value in the subject is in a target blood sugar range.

The method optionally further comprises i) the subject receiving the insulin, insulin analog or insulin mimetic in accordance with the intended insulin unit value and ii) the subject receiving food containing a number of food units in accordance with the balance value.

The carbohydrate unit is variable, but optionally comprises about 16 g of carbohydrate. The food unit comprises toast or bread including about 16 g of carbohydrate. The food unit is preferred because it is easier for a diabetic person to think in terms of food rather than in terms of grams of carbohydrate. Other numbers such as 14 g, 15 g or 17 g could also be used.

In one application of the invention, i) the subject provides a time schedule for periodic, divided intake of the intended insulin unit value or the intended standard food unit value and ii) the balance value is determined according to a time schedule for the subject to intake insulin units or food units needed to balance with the provided unit value and maintain blood sugar in the subject in the target blood sugar range during the time schedule.

The method optionally further comprises determining whether the subject did intake the intended food and insulin according to the time schedule and, if the subject did not intake the intended food and insulin, then adjusting the ending blood sugar value.

The method optionally further comprises increasing or decreasing future insulin units or food units so that the ending blood sugar value is in a target blood sugar range. If the subject did intake the intended food and insulin according to the time schedule and there is over a 25 point difference between the ending blood sugar value and the actual blood sugar value, then increasing or decreasing future insulin units or food units so that the ending blood sugar value is in a target blood sugar range.

The method optionally may further comprise repeating steps a)–c), wherein the starting blood sugar value in repeated step a) is i) determined by using the ending blood sugar level value determined in the prior step c) as the starting blood sugar value or ii) determined by measuring a subject blood sugar. The method optionally further comprises repeating steps a)–c). The method optionally further comprises determining the difference in actual subject blood sugar value and ending blood sugar values at a plurality of time intervals.

The insulin, insulin analog or insulin mimetic may be administered in at least two to five daily doses. The daily doses optionally comprise administering insulin in a morning daily dose and an evening daily dose.

The method may further comprise:
 a) entering the starting blood sugar value in a timetable
 b) determining the amount of carbohydrate to be ingested as food units and entering the number of food units in the timetable;
 c) determining the total amount of sugar in the food units and the sugar release rate value per unit of time and entering in the timetable the total amount of sugar and the sugar release rate value per unit of time;
 d) determining the balance value as the number of balancing insulin units to be administered to the subject to balance the total amount of sugar in the carbohydrate units and entering the number of insulin units in the timetable;
 e) determining the total sugar removal value and entering the value in the timetable;
 f) determining the sugar removal rate value per unit of time after administration of insulin, insulin analog or insulin mimetic and entering the sugar reduction rate value per unit of time in the timetable;
 g) determining an ending blood sugar value for each unit of time and inserting the ending blood sugar value as the starting sugar value for the following unit of time.

The method optionally further comprises:
 h) entering the starting blood sugar value in a timetable
 i) determining the amount of insulin, insulin analog or insulin mimetic to be ingested as insulin units and entering the number of insulin units in the timetable;
 j) determining the total sugar removal value to be caused by the insulin units and the sugar removal rate value per unit of time and entering in the timetable the total sugar removal value and the sugar removal rate value per unit of time;
 k) determining the balance value as the number of balancing food units to be administered to the subject to balance the total amount of sugar removed by the insulin units and entering the number of food units in the timetable;

l) determining the total sugar release value and entering the value in the timetable;

m) determining the sugar release rate value per unit of time after intake of food units and entering the sugar release rate value per unit of time in the timetable;

n) determining an ending blood sugar value for each unit of time and inserting the ending blood sugar value as the starting sugar value for the following unit of time.

In the above the timetable typically comprises a matrix, with one axis of the matrix having fields representing units of time and the other axis of the matrix having a plurality of fields with a filed representing units selected from the group consisting of starting sugar, carbohydrate units, sugar release per unit of time, insulin units, sugar reduction value per unit of time and ending blood sugar.

The total amount of sugar in the carbohydrate units can be determined by multiplying the number of carbohydrate units by the amount of sugar in each carbohydrate unit. The ending blood sugar value can be determined according to the formula: ending blood sugar value=starting blood sugar value plus total sugar release rate per unit of time minus sugar removal rate value per unit of time.

For an unknown carbohydrate food, the total sugar release value can be determined by measuring the increase in blood sugar after ingesting a food; determining the rate at which the carbohydrate in the carbohydrate source is ingested; wherein the rate is periodically measured over at least 3 hours after the food is ingested.

The balance value to be administered can be determined by multiplying the number of food units by the number of insulin units needed to balance the total sugar release value increase caused by one food unit.

If the subject blood sugar level increases instead of decreasing in the first blood sugar measurement following administration of a dose, a replacement dose is typically administered. If the amount of food units actually ingested in a day exceeds the intended food unit value, an additional dose of insulin is typically administered to the subject. If the amount of carbohydrate actually ingested in a day exceeds the intended food unit value, typically, no additional insulin is administered, and the actual blood sugar level is reduced the following day by increasing the amount of insulin administered in a first dose or by reducing the amount of ingested food units.

If the subject blood sugar value in the evening is higher than the target blood sugar range it is optionally untreated with additional insulin in order to avoid a low blood sugar condition in the following morning.

The starting blood sugar value or the ending blood sugar value is optionally adjusted to account for endogenous sugar production in the subject. The starting blood sugar value or the ending blood sugar value is optionally adjusted to account for a residual insulin effect.

The number of food units in the timetable chart are optionally redistributed to other hours when the subject changes the intake times of food units during the day.

If the subject intends to intake additional food units, then additional insulin units are administered to the subject to remove the additional food units.

If the subject intends to take additional food units for a specified time so the subject preferably ingests less food units at a time later in the timetable.

The correlation between carbohydrate units and insulin units is optionally adjusted according to the subject's weight, health and/or exercise.

The method optionally comprises determining how many food units are in a UC food by determining the effect on blood sugar following food intake with the following formula: blood sugar after food intake plus number of food units removed by insulin over two to four hours minus starting blood sugar and then dividing by the total number of blood sugar points in one food unit. The method also optionally comprises determining the amount of blood sugar increase in a subject after intake of a food unit and rate of blood sugar increase are determined according to the following formula: determining starting blood sugar in the subject; intake of a food item including one carbohydrate unit; and measuring the blood sugar in the subject periodically for at least 3 hours.

The method also optionally comprises determining the insulin effect on blood sugar removal according to the following formula: administering at least one unit of insulin to the subject; and measuring the blood sugar in the subject periodically for at least 3 hours.

Preferably, in the method, the target blood sugar range is beneath the renal threshold level. A suitable target blood sugar range optionally comprises 108–144.

Another aspect of the invention relates to a method of calculating food and insulin doses for a diabetic subject, comprising:

a) providing an intended insulin unit value or an intended carbohydrate unit value representing the amount of insulin or carbohydrate intended for intake by the subject;

b) determining the balance value of either insulin units or carbohydrate units needed to balance with the provided unit value and maintain blood sugar in the subject in a target blood sugar range;

c) displaying the number of balancing insulin units to the subject.

The intended food unit value is optionally provided in the form of a food for which the number of food units are retrieved from a data source, such as a database, indicating the number of food units in the food. The method optionally further comprises providing an alert when the database does not include a number of standard food units corresponding to the food. The methods and apparatus of the invention optionally use an algorithm or variant thereof described in this application.

The method optionally further comprises displaying to the user in a timetable the first blood sugar value, the carbohydrate unit term, the total amount of sugar in the carbohydrate units, the sugar release value per unit of time, the total sugar reduction value, the hourly sugar reduction value, the ending blood sugar value per unit of time or the starting sugar value. The method optionally further comprises providing an alert when the ending blood sugar value or actual blood sugar value of the subject is not in a target blood sugar range.

Another embodiment of the invention relates to an apparatus for calculating food and insulin doses for a diabetic subject, comprising:

a) input means for receiving an intended insulin unit value or an intended carbohydrate unit value representing the amount of insulin or carbohydrate intended for intake by the subject;

b) means for determining the balance value of either insulin units or carbohydrate units needed to balance with the provided unit value and maintain blood sugar in the subject in a target blood sugar range;

c) means for displaying the number of balancing insulin units to the subject.

Although letters are often used to denote steps above, such letters do not indicate a mandatory order in which to carry out the steps.

DETAILED DESCRIPTION OF THE DRAWINGS

FIG. 1 Table showing balance of toast, blood sugar and insulin.

FIG. 2 Table showing balance of toast, blood sugar and insulin. Insulin activity is considered over time.

FIG. 3 Table showing imbalance of toast, blood sugar and insulin if insulin and sugar are considered to act immediately. Insulin activity cannot be considered without considering its effects and activity over time.

FIG. 4 Table showing amounts of toast, blood sugar and insulin. Sugar release from toast and insulin activity are considered over time.

FIG. 5 Table showing amounts of toast, blood sugar and insulin.

FIG. 6 Table showing amounts of toast, blood sugar and insulin.

FIG. 7 Table showing amounts of toast, blood sugar and insulin when multiple toasts are ingested at different times during the day.

FIG. 8 Table showing allocation of toasts during the day.

FIG. 9 Table showing allocation of toasts, blood sugar and insulin during the day.

FIG. 10 Table showing allocation of toasts, blood sugar and insulin during the day.

FIG. 11 Table showing allocation of toasts, blood sugar and insulin during the day.

FIG. 12 Table showing allocation of toasts, blood sugar and insulin during the day.

FIG. 13 Table showing allocation of toasts, blood sugar and insulin during the day. The first insulin shot was increased to 18 and the second shot was decreased to 4. The 9:00 pm snack was moved to 10:00 pm.

FIG. 14 Table showing allocation of toasts, blood sugar and insulin during the day. The chart tracks the effect of 2 whole-wheat toasts and tea.

FIG. 15 Table showing allocation of toasts, blood sugar and insulin during the day. The figure shows the effects of a 3 toast lunch meal. Assuming that his 3 toasts are complex carbohydrates, he would add 63 points per hour.

FIG. 15b Table showing allocation of toasts, blood sugar and insulin during the day. The figures show a 3-toast dinner and the second shot of insulin the planning chart calls for.

FIG. 15c Table showing blood sugar during the day. The figures show a 3-toast dinner and the second shot of insulin the planning chart calls for.

FIG. 16 Table showing allocation of toasts, blood sugar and insulin during the day. The patient got up at 8:00 am. His blood sugar was measured and found that it was at 144 on the scale. So 144 is entered in the "Start Blood" column at 8:00 am.

FIG. 17 Table showing allocation of toasts, blood sugar and insulin during the day. The table shows a situation that required an extra dose of insulin.

FIG. 18 Table showing allocation of toasts, blood sugar and insulin during the day. The chart starts out like that in FIG. 17, but assumes that the patient can get by without as much food in the afternoon and evening, after a big lunch.

FIG. 19 Table showing allocation of toasts, blood sugar and insulin during the day. The meal of UC comes in the evening and is accommodated, as shown in the table. The patient's 4:00 pm insulin dosage is increased to 10 units, from its usual 4.

FIG. 20 Table showing allocation of toasts, blood sugar and insulin during the day.

FIG. 21 Steps for measuring blood sugar in response to ingesting toast and taking insulin. Two toasts added 108 blood sugar units to the body. To find out the exercise effect, repeat the 8:00 am to 11:00 am part of the experiment, exercise during the morning, and find out the difference, at 11:00 am, between blood sugar after exercise, and that measured in the prior experiment.

FIG. 22 Determining effects of exercise on blood sugar. The chart shows an abbreviated version of FIG. 21, which shows how to find the personal exercise effect.

FIG. 23 Table showing allocation of toasts, blood sugar and insulin during the day. Step by step approach to the DSS method.

FIG. 24 Table showing allocation of toasts, blood sugar and insulin during the day. Fast-acting insulin waited an hour, before "kicking in".

FIG. 25 Table showing allocation of toasts, blood sugar and insulin during the day.

FIG. 26 Table showing allocation of toasts, blood sugar and insulin during the day. The table illustrates the results after adjusting the pre-dinner dose from 6:00 to 7:00 pm.

FIG. 27 Table showing allocation of toasts, blood sugar and insulin during the day.

FIG. 28 Determining effects of toast and insulin on blood sugar.

Figure 29B:
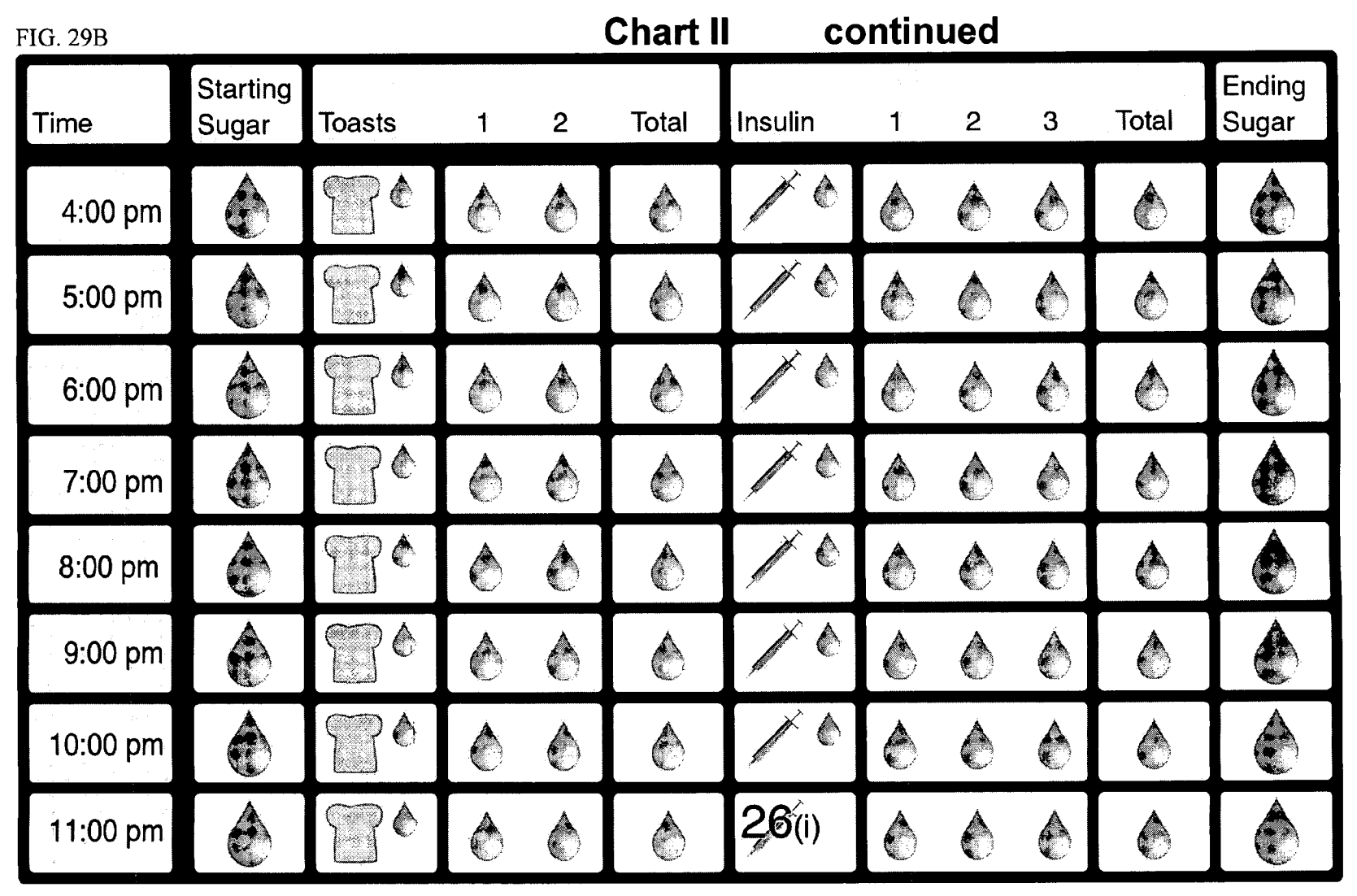

FIG. 29 Chart showing toasts, blood sugar and insulin.

FIG. 30 Determining effects of exercise on blood sugar.

Figure 31B:
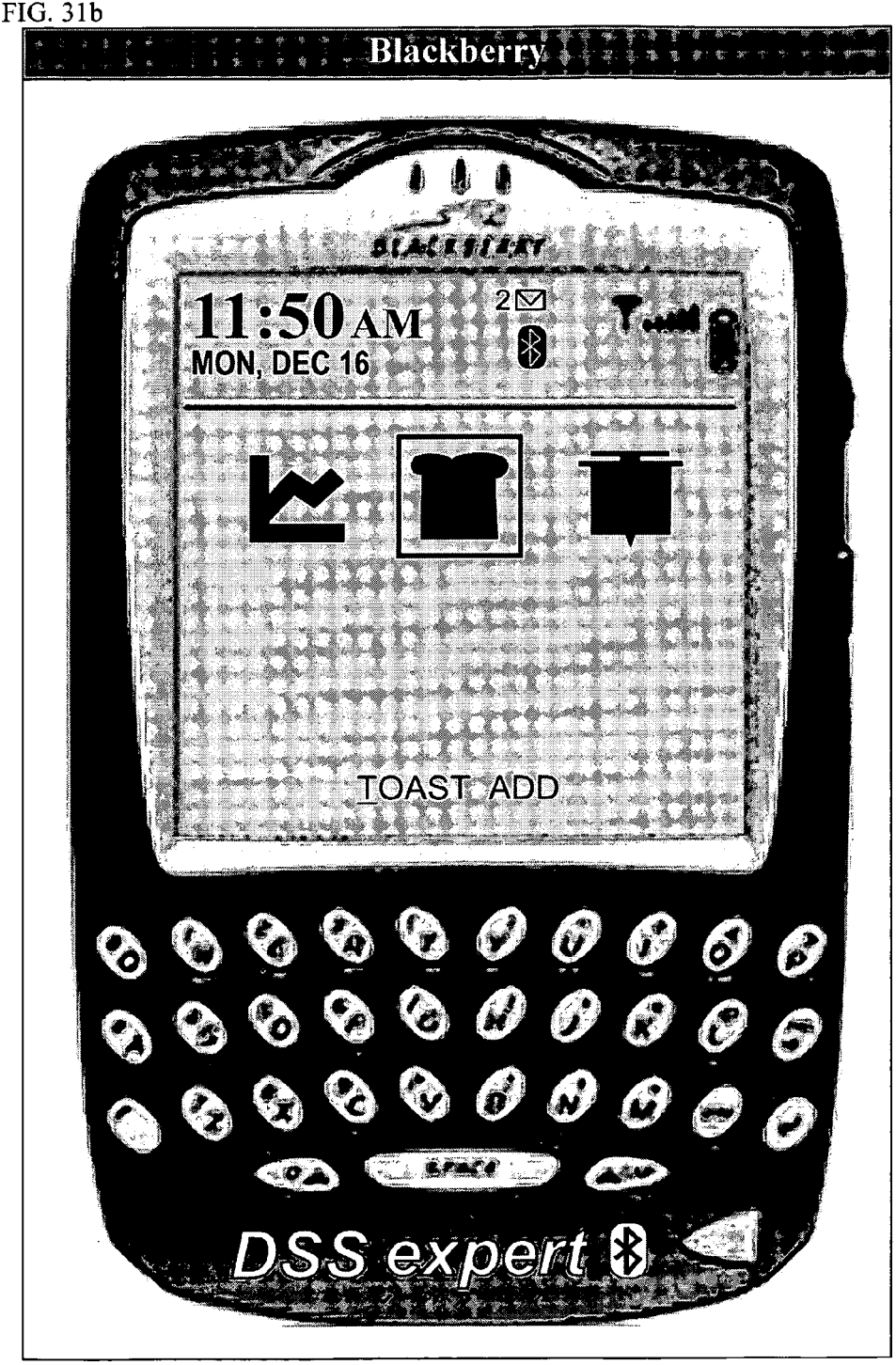
Figure 31C:
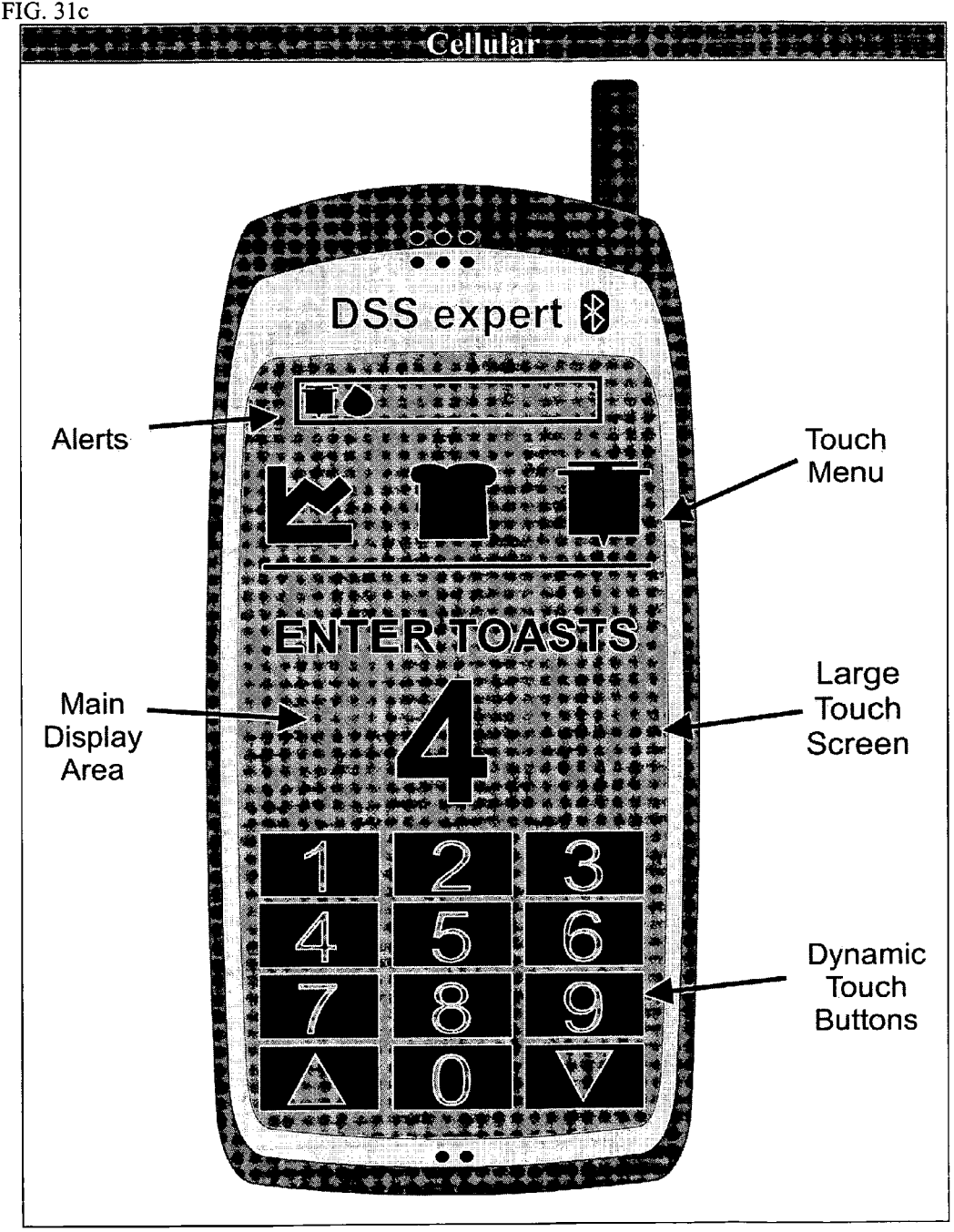
Figure 31D:
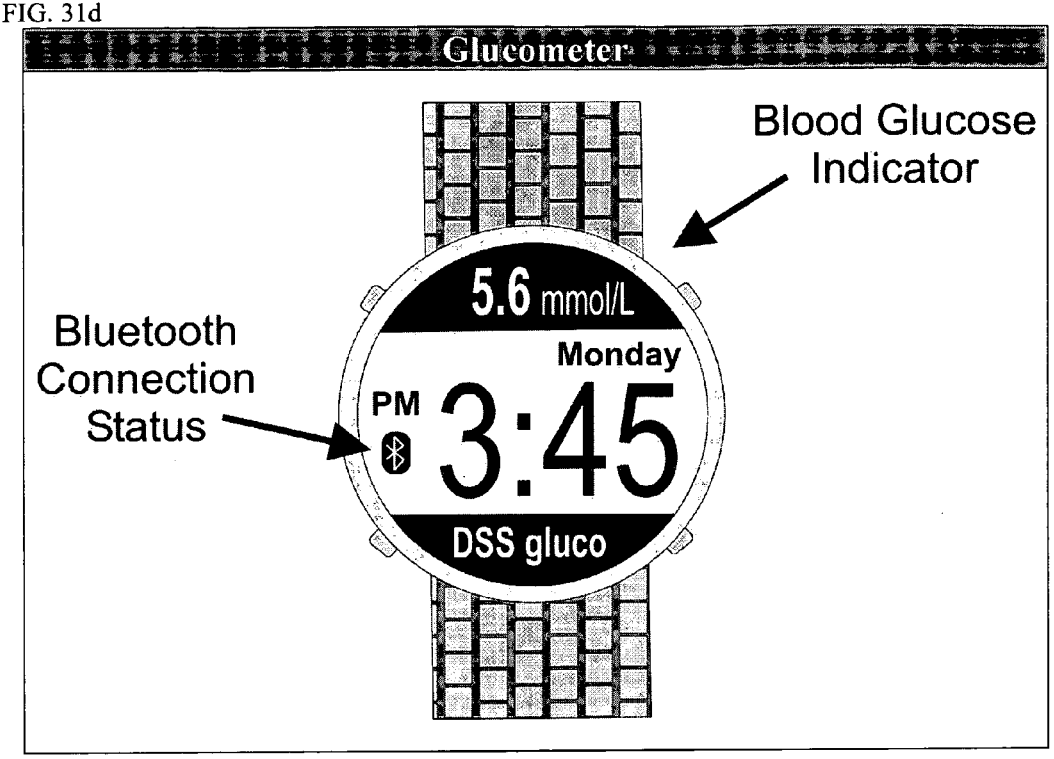
Figure 31E:
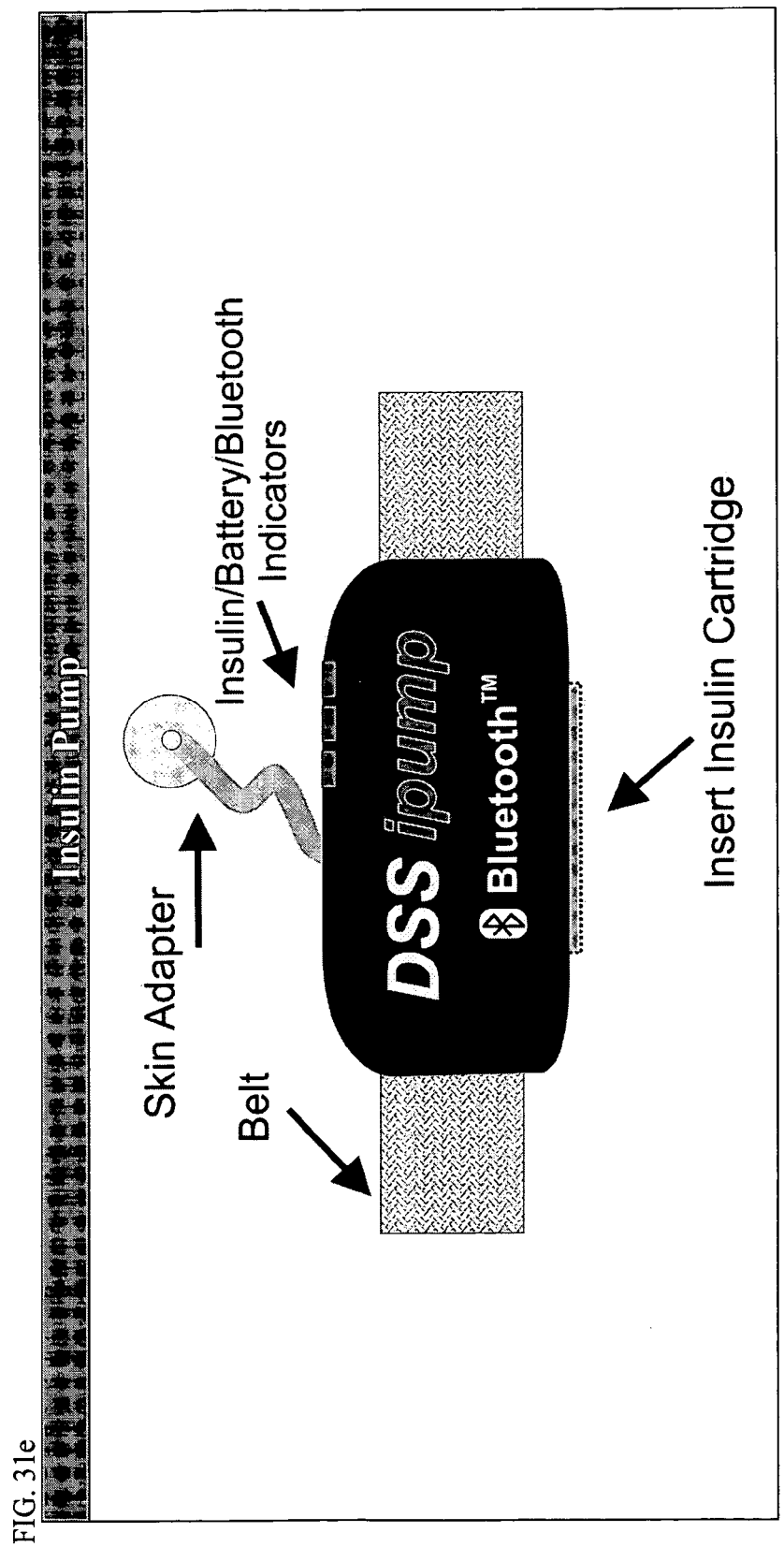

FIG. 31(a) to (e) show examples of devices implementing the methods of the invention. (a) shows a generic screen for a device, (b) shows a device (eg. a wireless device) having a keyboard as a user interface, (c) shows a cellular telephone with the keypad as an interface (d) shows a glucometer and (e) shows an insulin pump.

DETAILED DESCRIPTION OF THE INVENTION

"Diabetes" is preferably diagnosed when the blood sugar levels are higher than an accepted normal range. According to CDA (Canadian Diabetes Association) standards, diabetes onset occurs when a subject has a fasting blood glucose level over 7.0 mmol/L, or a random (anytime of day) sugar that is greater than 11.1 mmol/L. Once diagnosed, any effort/means made to the patient, in order to combat the hyperglycemia, is treatment, rather than prevention.

Many patients take synthetic insulin, preferably human insulin, which is prepared from genetically engineered cells. Insulin may also be isolated from the pancreases of pigs or cattle. The chemistry and structure of insulins are well known in the art.

The term "mimetic" as used herein refers to proteins, polypeptides or peptides that mimic the effect of insulin. These mimetics often have a structure that differs slightly from human insulin, for example, by one or two amino acids to change onset and peak of action. They all have the common property of causing removal of blood sugar (as measured with known assays). Some common insulins and mimetics (showing onset, peak and duration of action) are described below.

| Type of Insulin | Onset | Peak | Duration |
|---|---|---|---|
| Rapid-acting | | | |
| Humalog (lispro): Eli Lilly | 15 min | 30–90 min | 3–5 hours |
| NovoLog (aspart) Novo Nordisk: | 15 min | 40–50 min | 3–5 hours |
| Short-acting (Regular) | | | |
| Humulin R Eli Lilly: | 30–60 min | 50–120 min | 5–8 hours |
| Novolin R Novo Nordisk: | 30–60 min | 50–120 min | 5–8 hours |
| Intermediate-acting (NPH) | | | |
| Humulin N Eli Lilly: | 1–3 hours | 8 hours | 20 hours |
| Novolin N Novo Nordisk: | 1–3 hours | 8 hours | 20 hours |
| Humulin L Eli Lilly: | 1–2.5 hours | 7–15 hours | 18–24 hours |
| Novolin L Novo Nordisk: | 1–2.5 hours | 7–15 hours | 18–24 hours |

Intermediate- and short-acting mixtures
Humulin 50/50
Humulin 70/30
Humalog Mix 75/25
Humalog Mix 50/50
Eli Lilly
Novolin 70/30
Novolog Mix 70/30
Novo Nordisk The onset, peak, and duration of action of the above mixtures would reflect a composite of the intermediate and short- or rapid-acting components, with one peak of action.

| Long-acting | | | |
|---|---|---|---|
| Ultralente Eli Lilly: | 4–8 hours | 8–12 hours | 36 hours |
| Lantus (glargine) Aventis: | 1 hour | none | 24 hours |

Source: FDA Consumer Magazine; January-February 2002

Some types of insulin can be combined in a syringe. Other types must be injected individually.

Accordingly, it is contemplated as being within the scope of the present invention to use compounds that affect the regulation of blood sugar through the use of either naturally-occurring amino acids of insulin, amino acid derivatives, analogs or non-amino acid molecules capable of being joined to form the appropriate backbone conformation. A non-peptide analog, or an analog comprising peptide and non-peptide components, is sometimes referred to as a "peptidomimetic", to designate substitutions or derivations from peptides found to be active, which possess the same backbone conformational features and/or other functionalities, so as to be sufficiently similar to the active peptides to regulate blood sugar.

The use of peptidomimetics for the development of high-affinity peptide/protein analogs is well known in the art (see, e.g., Zhao et al. (1995), Nature Structural Biology 2: 1131–1137; Beely, N. (1994), Trends in Biotechnology 12: 213–216; Hruby, V. J. (1993), Biopolymers 33: 1073–1082).

One carbohydrate unit represents 100 calories and will add approximately 54 points to the diabetic's blood sugar (this number will vary for each individual). It is important to note that different foods convert to blood sugar at different rates, and that exercise also plays a role in the absorption of blood sugar. Exercise acts like insulin to absorb sugar from the blood. Total accuracy in estimating the food intake is not critical, and, in the method of the invention, estimates of food intake become self-correcting.

A preferred way to show carbohydrate units is to portray them as food units, such as a slice of toast or bread. This provides an easy way for patients to relate to the units. It is often difficult for patents to think in terms of carbohydrate units or grams of carbohydrate. These patients often more easily relate to food in food units, such as toast. Below is a list of the carbohydrate content of some common foods in conventional carbohydrate units and food units (toast). In this application, the term "toast" will often be used as an example, however other food units or carbohydrate units could also be used.

Foods, Carbohydrates and Carbohydrate Units
The symbols below illustrate the method,

| Food | Size | Weight (grams) | CHO (g/serving) | Toasts |
|---|---|---|---|---|
| Apple | Med | 140 | 18 | ☐ |
| Orange, large | 1 | 170 | 15 | ☐ |
| Cherries, large | 15 | 115 | 15 | ☐ |
| Fruit cocktail, canned, unsw. | ½ cup | 115 | 15 | ☐ |
| Peach, canned, unsw, | ½ cup | 115 | 14 | ☐ |
| Corn, canned | ½ cup | 85 | 15 | ☐ |
| Whole Wheat toast | 1 slice | 35 | 16 | ☐ |
| French baguette | 1 slice | 30 | 15 | ☐ |
| Peanuts, roasted | ½ cup | 70 | 16 | ☐ |
| Yoghurt, plain unsw. | ½ cup | 225 | 16 | ☐ |
| Cookies, oatmeal | 1 cookie | 26 | 16 | ☐ |
| Cookies, shortbread | 3 small | 25 | 16 | ☐ |
| Ice Cream, 10% fat, van. | ½ cup | 60 | 16 | ☐ |
| Marmalade | 1 tbs | 30 | 17 | ☐ |
| Potato, red skinned, mash | ½ cup | 115 | 16 | ☐ |
| Potato, white skinned, mash | ½ cup | 115 | 20 | ☐ |
| Grapefruit juice | 1 cup | 225 | 22 | ☐ |
| Baked beans | ½ cup | 115 | 24 | ☐ |
| Melba toast | 6 pieces | 30 | 23 | ☐ |
| Muffin, blueberry | 1 | 55 | 27 | ☐ |
| Shredded Wheat | 1 piece | 30 | 23 | ☐ |
| Cheerios | 1 cup | 30 | 23 | ☐ |
| Jelly beans, large | 10 | 30 | 26 | ☐ |
| Bran flakes | ⅔ cup | 30 | 22 | ☐ |
| Tomato soup, canned | 1 cup | 255 | 33 | ☐ |
| Pizza, cheese/tomato | 1 slice | 115 | 28 | ☐ |
| Donut, sugared | 1 | 45 | 29 | ☐ |
| Coca Cola | 1 can | 300 | 39 | ☐ |
| Rice, long grained white | 1 cup | 170 | 42 | ☐ |
| Spaghetti, white, cooked | 1 cup | 170 | 52 | ☐ |

I will illustrate a "toast" by using a toast symbol:
To illustrate "insulin" I will use a syringe:
To show sugar in the blood I will use the drop symbol:
The number of toasts is then put in the box, so 2 toasts are:
Four units of insulin are shown as:
The blood sugar reading is shown similarly, so blood sugar of 108 is shown as:

If a diabetic's morning sugar were 144:144, and he had 2 toasts, the diabetic needs to know how much insulin, he would need to get back to 144 in two hours." In this example, each toast adds 54 units of blood sugar, so 2 toast=108 blood sugar. So as we add 108 units of blood sugar, we have to take away 108 units to get back to where we started. If for the diabetic, 1 insulin absorbs 27 units of blood sugar, then 4 insulin will absorb 108. It will take 4 units of insulin to take away the 108 blood sugar added, and bring the diabetic's blood sugar back to 144."

If one used fast-acting insulin, that starts to work in one hour, and reaches its peak in 2 hours then assuming that the absorption rate of this fast-acting insulin is the same as for the intermediate-acting, (i.e. 1 unit of insulin for 27 units of blood sugar), the diabetic would need 4 units of fast-acting insulin to accomplish the task." (FIG. 2)

The longer acting the insulin, the more boxes you have to draw, and the longer the time-frame you have to plan for. (FIG. 3)

Ingested sugar and insulin do not have an instant effect. Neither food nor insulin acts instantly.
a) Look at how quickly the 'toast' becomes sugar. Assuming a normal glycemic index, food will convert to sugar in 2–3 hours, or 2 points per hour.
b) Secondly, the intermediate-acting insulin does very little for 2 hours, and then, like a time-release capsule, removes sugar at a rate of 27 blood sugar units for the next 6 hours. This is shown in the chart. (FIG. 4)
c) We calculate what our sugar is, by taking all the columns together.

The chart shows these considerations put together. For example from approximately 8:00 am to 1:00 pm the diabetic's sugar is high, and from 9:00 am to 11:00 am he is spilling the sugar. What if the diabetic wakes up with 144 blood sugar in the morning? One could give him the insulin 2 hours earlier. The results are shown in FIG. 5. This is better, but sugar is still higher than desired, for 8:00 am to 11:00 am.

One could consider eating toast 2 hours later. The result is FIG. 6.

That works the same, for the blood sugar, as moving the insulin back two hours. There is still high sugar between 10:00 am and 12:00 noon, so the diabetic might get hungry. If hungry one could give the patient protein or most vegetables since that won't likely impact his sugar. For example, the patient could have about 1 toast and an egg at 9:00 am, and another at noon. Eggs wouldn't count, so we can study the impact of eating 1 toast at 9:00 am, and 1 toast at 12:00 noon. (FIG. 7)

The patient is nourished, and has little high sugar. One could have also changed the insulin dose.

Once it is known how insulin works in the patient we can predict his sugar levels, while also monitoring carefully. After the patient has an idea how food and insulin interact, one needs to design a healthy diet for the patient: one that allows him to eat when others eat. It is not sufficient to have him eating to the insulin/sugar removal rate.

The invention figures out what the patient should eat, and design an insulin regimen that meets those needs.

Matching Diet with Insulin

In this section, the development of this diet for the patient, and the insulin strategy will be described. Trial-and-error was first used on paper, rather than in his body, to bring his blood sugar and food into balance with each other. In later sections, how to apply these techniques will be demonstrated. This diet and insulin strategy is called the DSS Method, short for "Don't Spill the Sugar".

Before going into the details of using the DSS Method, it is important to cover the four basic elements that need to be considered, in establishing a balance between blood sugar levels, insulin dosage and diet:
1. Design your diet
2. Match your insulin
3. Calculate changes to blood sugar
4. Adjust insulin Eating is not an exact science, so broad approximations will be used in order to get the message across. Although different types of bread may have different caloric content, it can be assumed that a toast or its equivalent is equal to 100 calories. Similarly, 1 oz. of protein is also approximately 100 calories. So one slice of chicken and one slice of bread are about 200 calories. However, it is important for the insulin-dependant diabetic to consider what proportion of the diet will be starch, and what proportion will be protein. Insulin intake has to be matched to carbohydrate intake; protein and fat are preferably ignored.

If, for example, two units of insulin will take care of one toast or equivalent, then the diabetic has to know how many toasts he is planning to eat, in order to take the correct amount of insulin. Again, to make matters simple, let us say that an inactive person weighing 150 pounds needs approximately 1500 calories daily to maintain that weight. If he decides that he will have a diet made up of 70% starch, and others at 30%, then he must take sufficient insulin to take care of 70% of 1500 calories, or 1050 calories. That is, roughly speaking, 10.5 toasts. Proteins and fats are preferably ignored in this equation. One can look at the example of a typical day of a patient's sample eating, to see how to design his insulin dose, so it keeps his sugar in the normal range of 100–144, on our scale of 0–540.

An example of a pattern would be a toast at breakfast, a good warm lunch, and a very hearty dinner, with some small snacks in between. For example, if the diabetic was also mostly vegetarian, but would eat eggs and fish, as well as occasional chicken, the strategy for the insulin would be to provide two peaks: one at lunch, and one at dinner. In this example, he also weighed approximately 160 lbs, so he needed 1600 calories per day; and was not active. Since he was mostly vegetarian, 30% of his calories would come from fats and proteins, while 70% would come from starches. So the number of toast equivalents he should eat per day would be 70% of 1600, (1120) divided by 100 (approximate calories per toast or equivalent), or about 11 "toasts". Once again we will not concern ourselves with the fact that starchy vegetables contain sugar. All of this will come out in the method and can be easily adjusted.

The following pattern of 11 "toasts" was decided upon:

| | |
|---|---|
| 1 | At breakfast |
| 1 | 2 hours after breakfast |
| 3 | At lunch |
| 1 | 2 hours after lunch |
| 1 | 4 hours after lunch |
| 3 | At dinner |
| 1 | An hour before bedtime |
| 11 | Total number of toasts |

Insert those numbers in the chart. (FIG. 8)

Now we consider insulin. In the patient's case, if one unit of insulin absorbs 27 units of blood sugar, and one toast creates 54 points of blood sugar, then it takes 2 units of insulin per toast (54/27). Therefore the number of units of insulin that the patient must take is 11×2, or 22 units. Although other factors such as exercise, weight and fat play a role in this equation, the above concept is enough to balance insulin and food. As will be seen shortly, the method will automatically adjust for all of these elements, but knowing this one key relationship gives a compass for the entire exercise.

Now we need to match the insulin to the toast pattern. A single injection of 27 units in the morning will not give what is needed, namely two distinct peaks of activity, to coincide with the two big meals (the 3-toasters). Let us then try 2 injections, divided equally and spaced in such a way as to create the peak activities required. Assume a 2 hour delay before the insulin acts.

It is also necessary to add some information on nutrition. There are quick sugars and slow sugars. Let us assume that a slow sugar food takes 3 hours to be converted to sugar, versus 1 hour for a fast-acting sugar. Assume that the food the patient intakes is of the slow sugar variety, and divide it over the three hours after it is taken. Clearly, if a snack were a fast-acting carbohydrate, such a fruit juice, then it should be put in the chart for the hour the fruit is consumed, or in the next one. (Any variations balance out.)

The result is shown in FIG. 9, which shows the sequence of filling out the form.

Here the blood sugar is calculated, using the pattern set in FIG. 9. The simple formula for calculating the amount of sugar in the blood is (final) BLOOD SUGAR=(starting) BLOOD SUGAR+TOAST−INSULIN, and it can be assumed that at 8:00 am the sugar was at 108 on the 0–540 scale.

This example demonstrates the problem of simply taking two insulin shots per day, each two hours prior to the main meals. The patient would spend 17 hours with high blood sugar, with 11 of these in the spilled sugar condition. Basically, the blood sugar is not bad until 11:00 am, but then it rises to unacceptable levels until 3 o'clock the next morning. (FIG. 10)

Taking these shots at mealtimes will not make things any better. This can be demonstrated by the next example where the second shot is moved by two hours. The result is not much improvement. (FIG. 11)

Now we spend 13 hours in the spilled sugar condition, with a further 6 of undesirably high sugar. The typical diabetic will measure his sugar twice a day: once upon waking and once before going to bed. His readings for the first case would be 108 and 248 while the second case would be 108 and 309. The morning sugar is under moderate control because we balanced the toasts and insulin. However, during the day the control is poor, and the patient would be feeling extremely sleepy all day.

After routine trials one is able to balance the food and the insulin. For instance, we noticed in our examples that we ended up with high blood sugar during the day. So, the solution to that problem would be to increase the insulin on the first shot and lower the dosage on the second shot.

So let us simulate that alternative, by providing 15 units and 7 units in the two shots. This is shown in FIG. 12. The patient profile is looking better. 1 hour of spilling sugar, and a further 10 of high blood sugar: better, but still not good. The morning sugar was again 110, and evening 174.

As we discussed, there are many variables that affect blood sugar. The important point here, is that we start with an approximation in order to determine the initial dose as a starting point, then, in practice, it will be refined.

Before this, except for the readings we took, we had no idea of what was going on inside the body. The patient may be so sleepy during the day, and have low sugar episodes in the early morning. One could reduce the insulin intake on the second injection, move the 9:00 pm snack to 8:00 pm or increase the first injection, reduce the second, and add a snack. One could also take three injections instead of two. One can control the blood sugar, by matching the food eaten with the insulin taken.

An example adjustment could be to increase the first insulin shot to 18, decrease the second shot to 4, and move the 9:00 pm snack to 10:00 pm. The result is shown in FIG. 13.

The adjustments provided an almost normal set of sugar readings, with not a single hour spent in the spilled sugar condition. (The reading of 150 at 9:00 pm is over the desired 144, but not by much, and only for one hour, so it can be taken as acceptable, if not desirable.)

The above chart is perfect for a normal person, but for a diabetic it has some danger spots. For instance, when the sugar reaches 90, and the patient eats a snack a little late, the patient is in danger of going into a low blood sugar condition. In fact, there are five such potentially dangerous spots on our latest chart. Let's remember that a diabetic doesn't feel bad at all when the sugar is at 215, but passes out when the sugar is below 72.

Attempting a 'perfect' schedule would expose the patient to the risk of low sugar conditions. However, we can all see now that a good schedule can be achieved, and that the rest is just a matter of fine tuning, and dealing with the surprises that a living body will throw on a regular basis.

The First Day

The following example demonstrates how these general rules would be put into practice. The patient got up at 8:00 am. His blood sugar was measured and found that it was at 144 on our scale. So we enter 144 in the "Start Blood" column at 8:00 am, in FIG. 16.

Now we pick a target level at which we would like to keep his blood sugar level, such as 108–144, rather than the 72–126 range, to protect the patient from a dangerous low blood sugar condition that can occur below 72.

The first thing to realize is that since his blood sugar is already at the top of the target range, eating starch at this point would not be a good idea. Even one toast would move his sugar to 200 and that is almost spilling the sugar. Even if you take insulin right away, it will take approximately 2 hours to take effect. The strategy at this level would be to take insulin, but wait about 2 hours before having starch. If the patient is hungry, and can't wait 2 hours to eat, he can have some eggs or cottage cheese, with some very low-starch vegetables like celery or cucumber, and some tea or coffee. That will hold him until the insulin kicks in at about 10:00 am.

We gave the patient his insulin as we had worked it out back in FIG. 15, (18 unit at 8:00 am and 4 units at 4:00 pm), waited for 2 hours-10:00 am, and then checked the sugar again. It was still about 145.

We then gave him 2 whole-wheat toasts and tea. As per our calculations, over the next 3 hours the insulin should absorb approximately 162 points of sugar, while the toast would have input approximately 108 points. So, in two hours the sugar level should be his starting level of 144, plus the effect of 2 toasts (72), minus 108 for the insulin and that would equal 108 by noon. We took the patient's blood sugar level at noon. It was 108. Here this is shown in the chart, FIG. 14.

It was now noon. Again, looking at our chart, we saw that his sugar would be approximately 90 by 1:00 pm. At that point he could have a very good lunch: a 3 toast meal. Assuming that his 3 toasts are complex carbohydrates, he would add 63 points per hour. Since the insulin takes out 54 points per hour, in three hours he would add a net of 27 points to his 90, for a new total of 117 at 4:00 pm. See FIG. 15.

We could have played lunch a little more conservatively, with a 2 toaster at noon, and then had a small fruit (fast acting) two hours after lunch. The sugar reading would have been nearly the same, as shown in FIG. 16.

At this time we must start planning for a 3-toast dinner, and the second shot of insulin our planning chart calls for. Here we go back to FIG. 15, parts b and c.

What happens when the subject goes to restaurants to eat food such as Thai, Indian or Chinese? How will he know how many toasts there are in all of those complex foods?

Unknown Carbohydrate (UC)

In some cases, instead of eating a carefully measured 3-toaster the patient gets a plate full of unknown carbohydrate ("UC"; also called "GOOP"). We would still know what his sugar level was before he ate it and we would be able to measure his sugar afterwards. By comparing the effect of 'UC' on the blood sugar, we would be able to determine retroactively how many toasts were in the 'UC'. If the anticipated sugar level were different than planned, we would also be able to figure out what the "UC": contained.

For example, if his sugar before the 'UC' were 110 and the insulin were removing 36 points per hour, then if the sugar reading after 2 hours were, say, 216, then our equation would look like this:

Starting sugar=110, plus 'UC', minus 72 (36 points removed by insulin times two hours), equals new sugar reading of 216.

Therefore, the equation is 110+UC−72=216.

That makes UC=216+72−108=180.

That calculation tells us that UC was worth just over 3 toasts in two hours (remember that 1 toast is 54 points). Most carbohydrate foods register as blood sugar within 3–4 hours of ingestion, so we would have to take another reading 1–2 hours later in order to determine correctly the full toast equivalent UC.

In fact, this is a math puzzle with one unknown (UC), and our method would handle this issue. After a while, the patient could estimate UC based on experience. For example, he would learn that a plate of stir-fried Thai rice was roughly equivalent to 4 toasts, or that a potato curry was equivalent to 5 toasts. Once he started to become familiar with toast equivalents, he could adjust the portions.

Once the toast equivalent of the patient's favorite meals is determined it can be put into the daily sheet. Then he will have two choices. One would be to reduce the amount of UC, so that he can achieve the right amount of toast for the insulin taken. The other option would be to give more insulin to support the increased toast intake.

A sheet to correspond to a situation that required an extra dose of insulin is shown in FIG. 17.

This chart shows five toasts eaten at a meal, where three would normally have come. The original amount of insulin was insufficient to maintain the proper blood sugar level. As long as we know two hours in advance, that the big meal will be coming (remember that the patient's intermediate-acting insulin takes two hours to take effect) we could add four units of insulin to take up the slack. In spite of the big meal, while sugar goes high a couple of times, it is not spilt, shown in the chart at 10:00 am.

Even in this situation we have a choice. We can give an extra shot of insulin as shown above, or we can take our regular second shot earlier than planned and then cut back on the evening meal.

The latter option is recommended for the following reasons: First of all it is not pleasant for anybody to take an injection. So any method that reduces the number of injections is preferred.

The second reason is that extra toasts mean that the patient will gain weight, which is not good. Keeping a good weight is very important to a diabetic.

The third reason is that it complicates the formula, as one can see.

The next chart FIG. 18, starts out like that in FIG. 17, but where we assume that the patient can get by without as much food in the afternoon and evening, after his big lunch.

This way, the patient does not have to take an evening insulin shot at all, relying on the two earlier ones. He still takes his two "toasts" at 4:00 pm, to help balance out the heavy insulin intake earlier in the day, but instead of a 3 Toast meal at 7:00 pm and a 2 Toast meal at 10:00 pm, he takes one toast at 6:00 pm and another at 9:00 pm. After his unusually heavy meal at lunch he probably is not hungry.

At 9:00 pm we also get closer to the 72 reading. The patient is awake, however, and if he were to slip into hypoglycemia for a while, he could correct that with a glass of juice.

One interesting thing shown by balancing these charts is, that with extra intermediate-acting insulin, you cannot just adjust for one big meal; you should add extra snacks too, later, to keep counteracting the long-lasting effect of the extra insulin.

There is also a good possibility, that the meal of UC comes in the evening, for example with an invitation to dinner away from one's home. This can also be accommodated, as shown in FIG. 19. Here the patient's 4:00 pm insulin dosage is increased to 10 units, from its usual 4.

While this is not ideal, with five hours of undesirable blood sugar readings, only one of these is actually spilling sugar with an 207 reading, and the 147–150 readings are barely over the limit of 144. Note that the intermediate-acting insulin cannot handle the rather massive five toaster, without this large carbohydrate intake being evened out with an extra toast at midnight.

We cannot pull the insulin forward to 3:00 pm, because that would give an hypoglycemic incident at 5:00 pm. If we had chosen a 4:00 pm insulin dosage of 11, instead of 10, we would have spilled less sugar (a reading of 200 at 8:00 pm) and not gone over during the night at all, but would have spent the latter part of the night at a borderline, worryingly low, projected reading of 80 through the night.

So, while big meals are not healthy as a rule, the system can accommodate them as an exception, and once in a while a third shot can be given, and calculated as shown here.

Exercise

Most patients, however, will want to incorporate exercise into their health plans, especially when understanding that exercise drops blood sugar, as insulin does. So when you exercise, you need less insulin.

When a patient begins to apply the DSS Method to himself, he will incorporate his exercise into the system, so that he will keep his blood sugar in balance after exercise, too.

The First Night

The patient's condition in the morning was 144. The next step is to see if this can be improved. If he eats according to our schedule, he should wake up with his sugar at 108. If we have miscalculated by just one toast, he might have a morning episode. To be cautious one can plan for his morning sugar to be 180. To get the morning sugar up to 180 one can raise his sugar level by four points: give him the equivalent of one and one third toasts before he goes to bed, in addition to what the countdown sheet says.

After, following this advice, the patient woke up with his sugar at 125.

The Missing Points

Even though the system predicted a morning sugar of 180, 125 was satisfactory. However, this was a problem since it was not predicted. During the day, when all kinds of food were eaten and a lot of insulin taken, the system was accurate. At night, when no insulin was taken and no food was eaten, the prediction of 180 should have been pretty accurate. 160 or 200 was satisfactory. 125 was a concern. This reading did confirm that the evening sugar is preferably always higher than the target, so as to avoid a low blood sugar condition in the wee hours of the morning. A couple of hours of spilled sugar in the 200–250 range was probably a reasonable price.

To satisfy the scientific side of this equation, a 'residual effect' must be inserted into the equation. Some small amount of insulin stayed active during the night. To account for it in our countdown, it is postulated that there was an eight hour 'residual effect' of 7 units per hour, so that 8 hours×7 would equal 56 units of sugar, or approximately the 54 missing points.

For all practical purposes, assuming an additional 54 points of sugar were removed from the blood during the night proved to be sufficient.

The First Mistake

A patient may disrupt his routine by eating UC late.

In one example, as we prepared the patient's night plan, the sugar could be high, and we knew that the "UC" had not run its course. It would take another 2 hours before we knew the value of "UC". The patient's sugar was at 250. Remaining insulin effect, as well as the residual effect, was 72. If his "UC" added an extra 2 toasts, he would be at 290 all night, and we would have a lot of problems stabilizing the sugar from that level in the morning. To hit our target of 144 by morning, we would have to give the patient another insulin shot to account for an estimated 144 points of sugar. This meant 6 units of insulin to get a morning reading near 144. But what would happens if the "UC" were all fast-acting sugar, and there were no more sugar coming? The patient's morning sugar would be 40 or even 20. What if the "UC" was weighted towards the last 2 hours? Even with the additional 6 units, we would be struggling the next day. We decided on 6 units. Unfortunately, the patient did go into a low blood sugar reaction.

This reaction could have been avoided by having a substantial snack, if eating late. This is a good alternative since high sugar, on occasion, won't cause much harm, as long as we bring it down again quickly.

Sugar

Sugar is sugar, no matter what the source. If one eats a piece of white toast, which is mainly starch, the stomach will quickly convert it to sugar in the blood. The sugar also gets into the bloodstream as blood sugar. Once it is in the blood, sugar is sugar, no matter what its source. The only difference is whether it is 'quick' sugar or 'slow' sugar, as discussed in the previous chapters.

What is important to a diabetic is the total carbohydrate content of the meal; that is, when the meal is converted to sugar, how many points go into the blood, and at what speed?

The nice thing about our method is that you can take a portion of chocolate or ice cream, or any other favorite sweet, and measure its impact on our count, in the same way that we calculated the value of "UC". In this way, it is possible to plan your favorite sweets into a diabetic diet.

Sweets in a diabetic diet are no less strange than a "sugar-free", (really meaning no added sugar), fruit juice. A sugar-free fruit juice is all "fast" sugar, whether there is extra sugar added or not. We must remember that 16 gms of carbohydrate equal 1 toast, sooner or later.

The insulin-dependant diabetic, offers a clear window into the impact of different foods, emotional states, and exercises on blood sugar. So the one advantage a Type I diabetic has, is that he or she can measure the impact of a food, and manually counteract it with a measured dose of insulin.

The subject may wish to have a high carbohydrate treat, for example a doughnut. In order not to interfere with our normal routine and calculations, we decided to make the doughnut an 'extra', to be offset with an appropriate extra dose of insulin. We decided to analyze the doughnut in advance, instead of treating it as "UC".

A doughnut looks like a small bun. We pretended to slice it mentally, and figured we could 'cut' it into 3 toasts. Then there was the jelly, with more starch and sugar: another 2 toasts, we guessed. Then there was frosting on top: another toast. Sugar in the dough: another toast. The total estimate was 7 toasts. It was all quick sugar. But it contained a lot of fat to slow it down. In the end, we all felt that our estimate must be too high as this represented a full 60% of the patient's daily starch intake. So we arbitrarily cut it back to 5 toasts. So we gave the patient 10 extra units of insulin, and the patient had a doughnut. Our estimate was accurate, give or take a point, and our system took the doughnut in stride. But keep in mind, that the whole doughnut was extra, and therefore a gain in weight. To avoid this, doughnut cravings should be satisfied through toast substitution rather than insulin increase, just like a non-diabetic person would have to do, if they wished to maintain their weight.

Vanishing Insulin

The subject had a noticeable decrease in his drowsiness. He was more energetic. Prior to our system, he would encourage us to go out, while he stayed behind to sleep. Now, he initiated excursions, whether a walk, a show, or a restaurant. Also, his ulcers did not recur, and the old dark skin from previous ulcers began to lighten and look healthy. His daily sugar readings were averaging below 144. He now rarely spilled sugar.

We routinely measured his sugar, two hours after lunch. One day, instead of his sugar following our scientific pattern according to our countdown sheet, it began to climb out of control. This situation with the disappearing insulin further reinforces the need for regular testing. If, as in this case, we had not measured the sugar until night time, we would have had to stay up all night, and measure even more frequently. Five or six pricks a day was the price of control over the following months. We 'lost' the occasional shot, but reacted quickly to replace it. The first reading that went up instead of down, was the signal for a replacement shot. We never had a situation where the 'lost' insulin suddenly appeared to cause havoc.

Once it vanished, it literally vanished without a trace, just as It had that first day the insulin went missing.

The Turnover

After 3 months, we took the patient for blood tests, to see his long-term control. The new blood test showed only 7% (down from 12%). If you realize that the range of this reading is 4.5% to 20%+, 7% was an excellent reading, very close to normal. His average daily reading was 126–144: high normal.

Insulin Variation

It is difficult trying to control sugar level through diet and exercise. One will often try the pills and increase them with no visible effect. One may have it under control in the evening—around 125 points—eat nothing, and still get up in the morning with sugar at 180+. The body starts producing sugar early in the morning to counteract the fact that we don't eat all night. One can take another pill, such as Metformin, which slows absorption of sugar by allowing digestion to proceed to the lower colon. The pills often have unfortunate side effects, An endocrinologist may advise a patient to take 15 units of fast-acting Humalog with every meal, and 15 units of Humulin N at night (intermediate-acting) and see how it works.

A patient has to discover for himself how these insulins work. Neither the doctor, nor the insulin manufacturer, gives any indication about the quantity of insulin required per unit of blood sugar. A patient often only knows that the fast-acting insulin, Humalog, acted over a period of 4 hours, while the intermediate-acting Humulin-N lasted up to 24 hours.

In one example, a patient had a blood sugar of fast-acting Humalog and began to measure every 30 minutes to see the impact on blood sugar. A sudden drop did not occur for an hour. Then a drop of about 90 points in the next hour, and 35 points in the next. Almost nothing in the fourth. This type of information is not typically provided to patients.

Precise numbers are not given because of liability concerns. However, giving a person medicine, without explaining how it works, is far more dangerous then giving all possible information, with as many caveats as possible, before handing over the tools.

In an example, a patient experienced that with every 2 units of quick-acting Humalog sugar level was reduced by 18 points, and that the effect started after an hour, and stopped after 3 hours. So the total impact on sugar level was occurring over a period of two hours, with about 60% occurring in the second hour after injection and 40% occurring in the third hour.

One can calculate how many toasts are in a next meal, and then take enough insulin to take care of that amount. You do not have to worry about leftover insulin, until the next meal. This simplifies the equation for the countdown, and reduces the likelihood of unexpected low sugar due to the constant action of an intermediate- or long-acting insulin.

Thus the countdown outlined in The DSS Method is much simpler. Several examples are shown here, as we plan days to fit projected eating patterns, but here we show a chart an example of how the short-acting insulin is matched to meals. (FIG. 20)

The intermediate-acting Humulin-N was a slightly different issue. If a patient wasn't eating at night, he can't calculate the number of toasts needed to take care of the dose of insulin. The liver was supplying morning toast, in an unknown amount. This patient did not know when, and for how long the effect would be present. The patient had to discover by trial.

The patient took the 15 units of intermediate-acting Humulin-N the first night. Sugar at night was 125 and in the morning it was 180. The patient moved it up until the morning reading was the same as the night reading. That took 26 units of Humulin-N, the intermediate-acting insulin.

The patient's basic routine became to use fast-acting as required, bring the level down to six or seven before bedtime, and then to take 26 intermediate-acting units, to wake up with a reading of 108 or 126. The patient adjusts morning insulin dosage, so that it not only fits what the patient is about to eat, but also adjusts to counteract the first morning reading if that be a bit high or low.

It is not easy for doctors to prescribe an exact regimen, or alternative regimens, because they do not have an easy way to do it. It would require having the patient under constant monitoring, until a balance were struck. They would need to strike such a balance for each type of insulin regimen. Such close monitoring is not practical, and it is not easy to hand over to the patient an inexact methodology for trying different regimens.

The DSS Method in Use

The DSS is a dynamic insulin dosing system that matches insulin to food, or food to insulin, in such a way that blood sugar stays in a safe range. It prevents damage from high blood sugar levels.

Using this system allows the insulin-dependant diabetic more freedom of lifestyle, adapting to the changes in food and activity that come with an ordinary lifestyle. The system is self-correcting, so that if blood sugar gets a bit high or low after any given meal or snack, it is corrected with the next one.

The first half of Part II contains preferred rules and explains the DSS method.

Rules: outlines a strategy for understanding and controlling diabetes, simultaneously balancing food and insulin.

The Experiment: takes the patient through a dry run of learning about the effect of a "toast" on blood sugar, and the counteracting effect of insulin on that blood sugar.

A short extra section outlines how to extend the Experiment, to learn about the blood sugar effect of typical Exercise.

Planning your Day: takes you through a dry run of working the tables; there is a suggested Insulin pattern and the information to apply the values found by doing the experiment.

The second half of Part II is the Step-by-Step section, which is an example of how to apply the DSS method The Experiment: provides a checklist to work through. The experiment is performed to find the individual's patterns.

Planning your Day: provides a checklist to use the DSS tables and plan food intake and insulin requirements.

One looks at what is to be eaten, and determines the number of toasts this represents. With practice, this is not difficult.

Rules

A desired level of sugar is about 108–144. While the ideal range for health is 72–126, getting close to 72 puts the patient in danger of hypoglycemia, especially to be avoided during the night. In practice, though, 108–126 is very tight. Were a patient to monitor blood sugar every one or two hours, and eat foods only of precisely known "toasts", spread evenly over the day, it would be achievable. So we suggest a compromise between perfection and a normal life, and preferably settle for 108–144. Other ranges could be used.

Maintaining the desired level of sugar promotes a healthier lifestyle. The principle of the entire control program is to keep the sugar level in this 108–144 range, by adjusting the level of food or the level of insulin as required. Preferred rules follow.

Rules:

| Rules for Diabetics |
| --- |
| 1. Take your blood sugar readings regularly! |
| 2. Learn about toasts! |
| 3. What is the toast effect on you? |
| 4. Different insulin types react differently! |
| 5. What is your insulin absorption rate? |
| 6. Eat at the same rate as your sugar is being absorbed! |

Rule #1 Take Blood Sugar Readings Regularly

Measuring the current blood sugar level is easy: not pleasant for a lot of people, but necessary. It means having to prick a finger, and to deposit a drop of blood in order to get a reading from a device called a "glucometer First thing in the morning: Measure sugar on arising, to know the base level.

Before eating: Since that is the time that allows one to determine how many units to take. Measure sugar before any meal, as that is the only way to determine how much and what kind of food to eat.

Before taking insulin: Taking insulin without measuring blood sugar is like driving without looking to see where we are going. (Evidently, this will sometimes be at the same time as before eating.)

Before retiring at night: Measure sugar before retiring at night.

Rule #2 Learn How to Count Toasts

To work the system, consider what constitutes a "toast". The method talks about "toasts", rather than grams of carbohydrate, because people, find it easier to visualize toasts than carbohydrates. It proves easier to look at a meal and say, "That is a three-toaster", than "That is a 48 carbohydrater".

So what is a "toast"? A piece of toast preferably equals 16 carbohydrates, also written 1 CHO (carbohydrate unit). In the following tests, we will use an actual slice of dry, whole-wheat, toast. A small baked potato is one toast; a half cup of boiled rice is one toast; a cup of strawberries is one toast, a reasonably small fruit is one toast. These facts alone are actually enough to give you a good start at "toast counting". Once used to estimating food, one will convert between toasts and carbohydrates quite easily.

Basically, one is estimating the amount of sugar and starch in each meal, which will be balanced by the insulin taken before that meal. In this calculation, we ignore fats, proteins, and non-starchy vegetables. In the American diet, starch usually means potatoes, fruits, grains, and things made from grain, such a bread and pasta. Some of these are absorbed more quickly than others, but this will balance itself out, with our insulin, over the space of a few hours. In an extreme case, such as a meal of nothing but pasta (a long absorbing starch), covered with butter or oil (which slows absorption), the insulin could kick in before the carbohydrates were there to be absorbed, and we could be hypoglycemic until they did. As always, extremes are to be avoided by diabetics.

Complex carbohydrates (e.g., pasta, grains, beans) release sugar into the bloodstream more gradually than bread or fruit. Fruit can release sugar within 20 minutes, whereas pasta will take 3–4 hours. So, for example, 3 small fruits will raise sugar by 160 points within 1 hour, whereas 1 cup of pasta will raise sugar by 160 points over 3–4 hours. There are exceptions to these examples. For example, some fruits are absorbed much faster than others, and some processed cereals are even faster than some fruit juices Any diet guide will show the number of carbohydrates in any given food. After a little practice, one will become adept at estimating the toasts in a meal. Most people eat more or less the same things, most of the time, so one will recognize the toast value of most of meals, once it has been calculated a few times.

Rule #3 What is the Effect of a Toast on the Diabetic?

When an insulin-dependant diabetic eats one slice of dry whole-wheat toast, or its 16 carbohydrate/1 CHO equivalent, his or her blood sugar rises in response, and stays high until he or she injects insulin to counteract the eating of the toast.

The effect of the toast can vary in both strength and duration. This response needs to be calculated. The toast effect number consists of two parts: what is the total rise in blood sugar resulting from eating one toast and when this rise takes place. Typically, a toast will raise the blood sugar by 54 points, and it will do it over about 2–3 hours.

Learning the toast effect for a diabetic will be one of the keys that offers him a way of controlling his blood sugar. This will be the focus of the first half of the experiment.

Rule #4—Different Insulin Types Absorb Differently.

There are four types of insulin in general use today: fast-acting, intermediate-acting, long-acting and premix described above.

Fast-acting

This type of insulin starts activity relatively quickly, and is effective for only a short period. It typically starts to be active within about a half hour, reaches peak activity at 1 hour, and ends after 3–4 hours. Three fast-acting insulins are Regular, Semilente and Humalog.

Intermediate-acting

This type of insulin starts its activity 2–3 hours after injection, but peaks at 6–8 hours, and ends at 12–24 hours. Typically, ⅔ of its activity is from hour three, to hour 9 to 11, and ⅓ over the following 6 hours. Three intermediate-acting insulins are NPH, Lente and Humulin-"N". NPH insulin has a large "N" on the label. Lente insulin has a large "L" on the label. Humulin N, Novolin N and NPH are all the same thing.

Long-acting

This type of insulin starts its activity almost 8 hours after injection, with peak activity occurring from 8 to 22 hours after injection. The three long-acting insulins are Ultralente, Insulin glargine (called Lentus), and Protamine Zinc (PZI). Ultralente has a large "U" on the label; PZI has a large "P" on the label Premix This type of insulin is basically a combination of fast-acting and Intermediate-acting, sometimes with buffers, and available in variety of proportions, to give various patterns of delay and of peak activity. They can continue to be active for the anything from 10 to 28 hours.

These absorption rates are highly variable, and should act only as guidelines. Using the DSS method, one will be able to determine his own absorption rates, with the insulin that he is currently using. It is possible that after working with this method, one will be able to determine which type of insulin will suit him best. He may even wish to experiment with different types, to see which one gives him the control he requires, in order not to spill the sugar.

As can be seen from the DSS System, it is preferable where possible to match insulin directly to what is to be eaten, rather than taking Intermediate-Acting, Long-Acting or Premix, and then hoping that the food matches what the insulin is doing in the body.

Rule #5 What is Your Personal Absorption Rate?

Each person's body reacts uniquely to insulin. The body's absorption rate is the amount of blood sugar taken out, and the speed of this process. In order to find out an individual's particular rate of absorption, he has to become his own guinea pig, and perform an experiment. In order to limit the inconvenience of too many experiments, this one should be combined with the experiment to find out the effect of eating 1 toast on the blood sugar level. This experiment is the topic of the next section.

Each type of insulin has a different impact on the amount of sugar that will be absorbed. In order to determine the impact of each type of insulin, the experiment will need to be repeated to determine the rate of absorption for each type. Whether the diabetic uses injections or an insulin pump, he must still determine the dose required through this experiment. (The detailed experiment for a personal absorption rate is described elsewhere in this application.

In the example, the Intermediate-acting insulin that the patient was using absorbed sugar from his blood at the following rate:

Negligible in the first 2 hours

⅔ over the next 6 hours

⅓ over the following 6 hours

Rule #6 Eat at the Same Rate as the Sugar is Being Absorbed.

It is important to eat at the same rate as the sugar is being absorbed; this will allow the blood sugar to remain steady at the desired level. There is a simple equation for controlling blood sugar:

An equation for balancing sugar is: ss+t−i=es ss=starting sugar t=number of toasts eaten i=units of insulin taken es=end sugar reading In regard to eating, the patient has two questions to ask.

1. Are you happy with your weight?

2. What are your normal eating habits?

These are vital, in determining how much insulin to take. Let's say that he weigh 150 lbs. In order to maintain that weight he may need 1800 calories per day. (This is a guess; it differs by individual, and also by activity level; a half-hour workout on a cross-trainer uses up 400–500 calories, which has a clearly dramatic effect on an 1800 calorie diet.) A vegetarian's diet will be different from a standard diet, and this difference will result in a different insulin dosage. The more starches and sugars that make up a diet, the more insulin required.

Weight is important because it determines how much the diabetic is going to eat. This in turn affects the amount of insulin he must take, to stay in the target area (100–144). If he eats more, he has to take more insulin; if he eats less, then he must take less insulin. If he takes too much insulin, his blood sugar will be too low, and if he doesn't take enough, it will be too high.

If his sugar is too low (below 72), he must eat right away; fruit juice usually gives the fastest response. If his sugar is too high, he must take insulin. (If it nears 540, he should seek medical help immediately.) How much insulin to take, under different circumstances, is the key to the method covered in this patent.

Even a doctor cannot accurately tell you how much insulin to take, without doing some form of the experiment described below.

Finding your Toast Effect and Absorption Rate

This experiment is designed to find these two numbers personal to the diabetic:

1) the effect that a toast has on his blood sugar, and 2) the rate at which a specific insulin type reacts in him. These numbers are the key.

Knowing these numbers gives him the ability to work the tables and manage his diabetes.

Below is an example of a dry run of the experiment using the numbers for a sample patient.

The best time to perform the experiment is in the morning, before eating, and before taking any insulin.

There are five steps to this experiment. The results have been recorded in Chart I in the figures. See how each step has been filled in. Understanding how to find the right numbers from this experiment is fundamental to working the charts in the next section.

Keep in mind that the diabetic in effect is performing two separate experiments, one right after the other. The first half of the experiment will find the numbers comprising his toast effect. The second half of the experiment finds the insulin absorption rate. These numbers will be key to new freedom, and future continuous health.

The preferred tools needed for this experiment are:

1) Fast-acting insulin 2) an accurate glucometer 3) glucometer strips 4) two toasts: whole wheat, dry.

Step 1—measure your sugar with a good glucometer. Record the number.

Step 2—eat two toasts.

Step 3—measure your blood sugar every 30 minutes for 3 hours and record the results.

Step 4—take 12 units of fast-acting insulin.

Step 5—measure blood sugar every 30 minutes and record these results.

In the first half of the experiment, the toast effect is measured: how much and how fast the toasts show up in blood sugar.

In the second half, he injects insulin, doesn't eat, then determines his insulin absorption rate: how this reduces his blood sugar back to healthy levels, measuring how much effect the insulin has, and how fast.

If the experiment is repeated with intermediate-acting or fast-acting insulin, the diabetic will have to keep measuring for a longer period of time (probably 16 hours, or even 24 for long-acting) than shown here.

An example of what the results may look like is provided below. However, the diabetic's particular numbers are the ones that should be used in a given case.

The first half of this experiment shows the toast effect

First, we see that, over the 3 hours from 8:00 am to 11:00 am, the 2 toasts added 108 points to his starting blood sugar. (After three hours, it won't go up any more, at least not significantly.) Therefore 1 toast adds a total of 54 points over 3 hours. This is the total toast effect on the body.

Second, we see that, over the 3 hours from 8:00 am to 11:00 am, the blood sugar went up 36 points per hour, in response to 2 toasts. Therefore 1 toast adds 18 blood sugar points per hour for each of 3 hours. This is the hourly toast effect on the body.

These are the two results that comprise the toast effect.

The second half of this experiment shows the insulin absorption rate.

Third, we see that, over the 3 hours from 11:00 am to 2:00 pm, 12 units of fast-acting insulin took out 108 points of blood sugar. Therefore 1 unit of fast-acting insulin takes out a total of 9 (108/12) units of blood sugar. This is the total insulin absorption effect on the body.

Fourth, we see that, over the 3 hours from 11:00 am to 2:00 pm, the blood sugar went down 36 points per hour, in response to 12 insulin units. Therefore 1 insulin unit removes 3 (36/12) blood sugar points per hour for each of 3 hours. This is the hourly insulin absorption effect on the body.

These are the two results that comprise the absorption rate.

There is one further number that is important. This is the overall relationship between toast and insulin.

Fifth, from the whole experiment, we can see that, as blood sugar level both started and ended at 180, the total effect of toasts and insulin is neutral. He ate 2 toasts, and took 12 units of insulin, so 1 toast is balanced by 6 units of insulin. In our body, six units of fast-acting insulin balance the effect of one whole-wheat toast. This is the total balance between toast and insulin.

When performing the experiment, the formula to use in case your ending blood sugar is not the same as the beginning blood sugar is as follows:

The equation for balancing sugar is: $ss+t-i=es$
ss=starting sugar
t=number of toasts eaten
i=units of insulin taken
es=end sugar reading The patient's own numbers are the ones that count. Do not just take the ones given here, as his own may be quite different. Both carbohydrates and insulins affect different people differently.

This relatively simple experiment allows a diabetic to manage his blood sugar. It has established the relationship between food, insulin, and blood sugar for his unique body.

The Exercise Experiment.

The experiment can also be used to find out the effects of typical exercise, whatever that may be. Some people are so ill that just getting through the day is all the exercise that they are likely to get, but most of us benefit from regular exercise, and its effect on the blood sugar must be taken into account.

While insulin takes sugar out of the blood, exercise does the same. This makes sense, for sugar is the body's fuel, and exercise can be expected to burn up this fuel. When the diabetic plans his day, then, he needs to know how much less insulin to take (or more food) when he exercises.

How much blood sugar burns up in exercise is specific to the body, and to whatever exercise is done. Half an hour on a cross-trainer, or swimming lengths will effect the blood sugar differently from taking a walk for an hour. Furthermore, the way one walks may be very different from the way another person does, and the amount of sugar burned will vary, too. So each diabetic needs his own personal data.

If the diabetic has two (or more) typical exercises, such as swimming three days a week and walking the other four, he will have to do the exercise experiment twice, once for each typical exercise pattern.

In FIG. 21, above, he found that two toasts added 108 blood sugar units to his body, from 8:00 am to 11:00 am. (Line 8 minus line 1.) To find out the exercise effect, he will, on the morning of his choice, repeat the 8:00 am to 11:00 am part of the experiment, exercise during the morning, and find out the difference, at 11:00 am, between his blood sugar after exercise, and that measured in the Experiment above.

FIG. 22 is an abbreviated version of FIG. 21, which shows how to find you're the personal exercise effect.

Measuring every half hour is not necessary, although it may be of interest in seeing the body's pattern. The important figure is (Original result at 11:00–Original result at 8:00)-(Exercise result at 11:00–Exercise result at 8:00) FIG. 23, because that is the amount of blood sugar that exercise used up. In this case it is: (288–180)–(198–144), equals 108–54, equals 54.

In this example, the exercise used up 54 units of blood sugar. As we have established that, for the purposes of this example, one unit of insulin removes 9 units of blood sugar, we know that the next time we repeat this exercise we need to inject 6 (54/9) fewer units of insulin, at the injection before the exercise.

Alternatively, but less beneficial for both health and waistline, eating one extra toast would also counteract the effect of the exercise in this case.

A Suggested Insulin Pattern.

Since very fast-acting insulins, such as Humalog are on the market, and easy to use, they are in fact simpler and more flexible than any other system. Here is an example of how to take insulin. We suggest that a patient consult with a physician to determine if this option is available The greatest advantage to the diabetic with the DSS system, apart from not spilling sugar, and thus avoiding harm to his body, is that one can adjust as the day goes on. By taking insulin just before meals, one can take the correct amount for what is about to be eaten. A patient can eat less, when less hungry.

Here is the pattern:
1) He takes insulin before he eats: ranging from an hour before, to right as he sits down.
2) He figures out how many toasts are going to be in the meal.
3) He takes insulin to match, using the balance between toast and insulin "Fifth" in the experiment. (In the example, this was 6 units of fast-acting insulin for each toast)
4) Now, to make sure that the system is working as planned, he checks his blood sugar about three hours after each meal, before going to bed, and each morning on arising.
   Note: The blood sugar should be in the safe range (72–144) after each meal, (99–126 ideally), and it should remain near constant during the night.
   Note: If the blood sugar does not react as expected after several meals, the estimation of carbohydrates (toasts) may be inaccurate. If it is, the experiment on page 75 would need to be repeated.

Every evening on going to bed, the diabetic must take a specific number of units of intermediate-acting insulin, to take care of the residual effect or "background" sugar.

It is recommended that you check with your own doctor, to see if he or she concurs with this pattern. Even if the doctor prefers some other combination, of fast-acting and intermediate-acting, the DSS system will still work As the intermediate-acting insulin, taken each evening, has a background effect, it is not put into the calculations, except to make sure that the glucometer readings are in order each morning. If they are consistently too low, then the dosage of intermediate-acting insulin should be reduced: if too high, then increase it.

Planning Your Day

Calories, Carbohydrates, Absorption Rates

Here is a description of how to create a personal profile.

Working the Tables.

The DSS tables are how to plan the day. The keys are the numbers from the experiment: the toast effect and personal absorption rate. The following is a dry run through creating and using these tables.

Consider the sample table below, FIG. 24; there are a lot of different things to do, but each one is simple, and they can lead to good health.

Here is a step-by-step approach to the DSS method.
1) fill in the starting sugar, according to what the meter says at the time the chart is started.
2) fill in the number of toasts intended to be eaten, in the relevant time slots.
3) use the "total toast effect", and fill in the total effect of those toasts on the blood sugar, next to the toast symbol, in the same box.
4) use the "hourly toast effect", and put it into the next blood symbol, under "Meals 1". Add "Meals 1" and "Meals 2" together if two meals affect the same hour. Put the total meals effect under "Meals Total".
5) use the total balance between toast and insulin" to calculate how much insulin must be taken to balance the total blood sugar effect of each meal of toast(s), and fill that into the "Insulin" box for that hour.
6) use the "total insulin absorption" to calculate the total sugar effect of that insulin, and put that figure next to the Insulin symbol, in the same box.
7) use the "hourly insulin absorption" to fill in the other blood symbol, with the relevant reduction in blood sugar each hour, under "Dose 1". Add "Dose 1", "Dose 2", and "Dose 3" together, (if two or three meals affect the same hour), and put that figure under "Dose Total".
8) Use the formula, es=sis+t−i. Calculate the end sugar by adding the starting sugar and the toast effect, for each hour, and subtracting that hour's insulin effect.
9) Fill in the end sugar blood symbol, and carry it to the starting sugar in the next hour.

The result will look something like this, Example 1, FIG. 23. filling in the starting blood sugar, and the suggested insulin injections. In this example we are assuming that one unit of insulin absorbs 9 units of blood sugar, and that each toast adds 54 units of blood sugar, for the fast-acting insulin. The number toasts is therefore multiplied by 54 to give the relevant added blood sugar reading, and the insulin dosage is multiplied by 9 to give the relevant subtracted blood sugar reading.

EXAMPLE

Note that we put a reminder at 11:00 pm, to take the intermediate-acting insulin shot, discussed above, to last through the night.

Looking at these results, they present some problems. If the insulin starts to act, right as it is taken, the diabetic will be hypoglycemic (blood sugar under 72), from 6:00 to 8:00 pm.

Now one can see the advantage of having done the experiment, and of doing the tables. If in fact it was found in the experiment, that the fast-acting insulin waited an hour, before "kicking in", then the table would look like FIG. 24, Example 2.

The results are certainly better, for blood sugar values of 162 and 180 are certainly not severe, but this can be further improved.

To reflect the lag in your insulin having its effects, the dose before lunch can be moved an hour earlier. (FIG. 25)

It is not under the perfect 126 from 9:00 to 11:00 am, but it is very good indeed overall. If, on the other hand, going back to Example 2, the insulin in fact kicked in immediately, as it did in Example 1, then, the insulin would not be taken until the diabetic is ready to eat, Example 4 (FIG. 26) below, illustrates the results after adjusting the pre-dinner dose from 6:00 to 7:00 pm.

This demonstrates that an apparently small change in schedule, or in the time it takes insulin (or starches) to work, can have considerable effect on the blood sugar, and hence on health.

Example with Intermediate-acting Insulin.

To show that the DSS System works with other kinds of insulin, consider the next example, where the effect of insulin on blood sugar was calculated with intermediate-acting insulin, instead of fast-acting.

This pattern gives a lot less flexibility, in that once the intermediate-acting shot is taken, it has to be "covered" until it wears off. (FIG. 27)

This shows a not quite perfect day, with a slight overage at 8:00 pm after dinner, but it is very good, far better than would be expected with the "take your dosage and hope" technique so often used.

A patient will know, all day long, what his blood sugar is going to be. If his calculations show that he is spilling the sugar, then he can adjust either his food, or his insulin, keeping total caloric input in mind.

Keeping Healthy By Matching Food and Insulin

The following is a step-by-step method of balancing food and insulin intake.

Body weight, activity level, food eaten, illness, stress and insulin sensitivity or resistance all contribute to determining how much insulin is needed by an individual at a specific time. As lifestyle factors change, it is likely that insulin needs will also vary. The invention takes these factors into account in balancing insulin unit and food unit intake.

The experiment will first find out toast effect, absorption rate, and balance between toast and insulin. These numbers are the keys to using the DSS System. Then, these numbers will be inputted into the charts in order to plan a day.

The Experiment.
An example of the tools needed for this experiment are:
1) Fast-acting insulin
2) an accurate glucometer
3) glucometer strips
4) two toasts: preferably whole wheat dry.

The following are an example charts that a diabetic subject would use. The diabetic would check off each step as it is done.

Steps for Chart I (FIG. 28):
1. It is morning, before eating, before insulin.
2. Record present time in Chart I (below), line 1, (Time)
3. Fill in times in Chart I, (Time), lines 2 to 15, for next 6 hours
4. Measure blood sugar & record number in chart I, line 1, (Your Results)
5. Eat two (whole wheat dry) toasts.

6. After ½ hour, measure blood sugar, & record in Chart I, line 3, (Your Results).
7. After next ½ hour, measure blood sugar, & record in Chart I, line 4
8. After next ½ hour, measure blood sugar, & record in Chart I, line 5
9. After next ½ hour, measure blood sugar, & record in Chart I, line 6
10. After next ½ hour, measure blood sugar, & record in Chart I, line 7
11. After next ½ hour, measure blood sugar, & record in Chart I, line 8
12. Inject 12 units of fast-acting insulin
13. After next ½ hour, measure blood sugar, & record in Chart I, line 10
14. After next ½ hour, measure blood sugar, & record in Chart I, line 11
15. After next ½ hour, measure blood sugar, & record in Chart I, line 12
16. After next ½ hour, measure blood sugar, & record in Chart I, line 13
17. After next ½ hour, measure blood sugar, & record in Chart I, line 14
18. After next ½ hour, measure blood sugar, & record in Chart I, line 15
19. Subtract Your Result line 2 from Your Result line 8, and divide this result by 2 (for 2 toasts). This is the total toast effect. Total toast effect=(line8−line2)/2=_____.
20. Subtract Your Result line15 from Your Result line 8. Then divide this number by 12. This is the total absorption rate, for this kind of insulin. Absorption rate=(line8−line15)/12=_____.
21. Calculate the balance between toast and insulin. If the blood sugar started and ended at the same point, this is simply 2 toasts balance 12 insulin units, so 1 toast balances 6 insulin units. If not, the formula is: 1 toast is balanced by: (1/total absorption rate) times (total toast effect).
22. Review the blank working tables, during or after the experiment, in order to plan for the following day.
23. Take the insulin which would normally be taken at this time of day, so that the intake of starches and sugars at dinner time and snack time are looked after as well as to last through the night.
24. Take blood sugar readings each time before eating, and before going to bed, to monitor daily health.
25. Decide what will be eaten first thing the next morning.
26. Calculate the number of toasts in this breakfast. Remember:
   a small baked potato=1 toast.
   a half cup of boiled rice=1 toast.
   a cup of strawberries=1 toast.
   A small apple=1 toast
   1 toast=16 grams of carbohydrate.
   Any diet guide will have the number of carbohydrates in any given food.

Record the toast effect, absorption rate, and balance between toast and insulin for this type of insulin in this table, for future reference. There is more than one table for experiments that can be used with different types of insulin.

Type of insulin
Total toast effect
Hourly toast effect
Total insulin absorption rate -continued Hourly insulin absorption rate
Toast and insulin balance
Type of insulin
Total toast effect
Hourly toast effect
Total insulin absorption rate
Hourly insulin absorption rate
Toast and insulin balance
Type of insulin
Total toast effect
Hourly toast effect
Total insulin absorption rate
Hourly insulin absorption rate
Toast and insulin balance Steps for Chart II (FIG. 29)
28. Next morning.
29. Fill in determined values of toast effect (from step 20) and absorption rate (from step 21) into chart II
30. Refer to Charts II, a, b, and c, below.
31. Start at the present time, and fill it into the chart.
32. Measure blood sugar, and put the reading in the blood-drop under "Start Sugar", on the appropriate time line.
33. Fill in the number of toasts intended to eat at breakfast (figured out in Step 27, above) into the toast symbol for that time.
34. Multiply the figure in the toast by the toast effect (from step 20), and record it in the first red blood-drop next to the toast.
35. Decide if the toasts were immediate-effective (like fruit juice), or regular (we don't use this term in the application, I think we call them long-acting), (like grains, bread, potatoes, or other starches).
36. If they are immediate-effective, put all of this blood-sugar value into the second blood-drop under "Toasts". If they are regular, then divide it over 3 hours, and put that into the 3 blood-drops.
37. The blood-sugar value added to the body, shown in the first red blood-drop, is what has to be taken out by fast-acting insulin, (plus any excess in the starting blood sugar, if it were high, or minus any deficit in the starting blood sugar, if it were low.)
38. Take this value of blood sugar to be removed, and divide it by the absorption rate. This will determine how much fast-acting insulin needs to be taken, to balance the toasts eaten for breakfast.
39. Put this figure from Step 38 into the blue hypodermic, at the same time point that the toast will be eaten. (Note that this should be an hour earlier, if the insulin delays an hour.)
40. Multiply the insulin value in the hypodermic by the absorption rate, to give the total blood sugar taken out, and put in that value as a minus, in the first blood-drop next to the hypodermic.
41. Split this blood-sugar taken out into that hour, and the next two, putting one third of it into each second blood drop, again as a minus.
42. If the rate of insulin absorption for fast-acting insulin was shown in the experiment to be other than three hours, put in the values in 41 as the experiment indicated.
43. Calculate the End Sugar: Starting sugar plus Sugar added for that hour minus Sugar removed for that hour: put this value into the red blood-drop under "End Sugar".
44 Carry this value to "Start Sugar" for the next hour.
45. Continue on with this process, repeating Steps 32 through 44. If planning a diet in advance for the whole day, the whole chart can be set up in the morning. Alternatively, toasts and insulin for each meal or snack can be filled in as the day passes.
46. Before each intake of "toasts", remember to measure the blood sugar, and update the Start Sugar value with an actual value, rather than a calculated one.
47. If there is any substantial difference between the calculated value for Start Sugar, and the actual one, check these points:
   a) is there any calculation error?
   b) could the "toasts" have been estimated incorrectly?
   c) If the error is systematic, i.e. if it is consistently too high or too low, it may be necessary to repeat the experiment, Steps 1 through 21, to ensure that the right values for the blood effects of insulin (minus) and toasts (plus) have been used.
48. Whenever the blood sugar is measured before a meal, enter it in Start Sugar. When the insulin dosage is calculated in Step 38, and the chart is worked through to filling in End blood Sugar, it will automatically be evident whether this value is out of line, and the insulin dosage can be adjusted to keep End Blood Sugar in the safe range of 100–144.
49. Aim to keep the blood sugar level, recorded in N, in the safe range, 72–144: or, more realistically, 99–144, especially at night. (is the safe range 100 to 144 or 99 to 144 throughout application it is inconsistent)
50. Each evening, take a dose of intermediate-acting insulin on going to sleep, to take care of residual blood sugar entering the blood stream during the night.
51. The first night, either take the accustomed dosage of intermediate-acting insulin for the evening, or try a dosage around 20 units.
52. In the beginning, err on the side of too little intermediate-acting insulin, as higher blood sugar, (say a blood sugar reading of 215), is less of an incident, than a low blood sugar (such as a blood sugar reading below 72).
53. If in doubt, check the blood sugar reading once or twice during the night, to make sure that it is not too far out of range.
54. If the blood sugar goes a little too high during the night, take a bit of extra insulin with breakfast. However, if the blood sugar is too low, take the morning toast(s) without insulin, or with reduced insulin, to get back on course.
55. If the blood sugar goes too low during the night, have a glass of fruit juice, and check again in an hour or two.
56. In the morning, when arising, measure the blood sugar to see if it rose or fell during the night. If it rose, for example by 20 points, then 20 divided by the absorption rate for intermediate-acting insulin will determine how many more units of intermediate-acting insulin should be taken every night.
57. If the morning value dropped, for example by 10 points, then the absorption rate divided by 10 will determine how many fewer units of intermediate-acting insulin should be taken every night.
58. When the morning sugar value varies more than a bit from an ideal 110, the morning insulin dose will need to be adjusted to get the blood sugar back to 110, as well as to look after the first starch intake of the day. Divide the difference (between the actual blood sugar and 110) by the absorption rate for fast-acting insulin to get the difference in the number of insulin units to take, from what would have taken for the first "toast" Take more if the blood sugar is too high, less if too low. For example, if the morning blood sugar were 135, and the absorption rate is 6 blood sugar units per insulin unit, then (135−110)/6=4.2 more units must be added to the morning dose, which in this example would go from 12 to 16.
59. Put the actual insulin dosage, and actual "toasts" into the chart for the new day.
60. In addition to counting toasts, keep track each day of the total calories, so that weight does not get out of hand.

Exercise.

This is a supplementary experiment, to find out how to allow for the effects of a typical exercise routine on blood sugar.

Steps for Chart III (FIG. 30):
X1. It is morning, before eating, before insulin.
X2. Record present time in Chart III (below), line 1, Column B
X3. Fill in times in Chart I, (Time), lines 1, 2, 3 and 5, to match the times in the original experiment.
X4. Fill in the results obtained in the original experiment for starting sugar, and sugar after three hours, (line 1 and line 8 in Chart I) in the Original Results column on line 1 and line 5.
X5. Measure the present blood sugar & record number in chart III, line 1, column Exercise Results.
Note: If the blood sugar is low at this point, it is not a good day to start exercising, since exercise might put a diabetic at risk of hypoglycemia. An ideal starting reading would be in the range of 125–180.
X6. Eat two (whole wheat dry) toasts.
X7. After ½ hour, begin exercising, which will typically last ½ to 1 hour.
X8. After exercising, continue with normal activities. Do not take the blood sugar immediately, because the effect of exercise, like that of insulin, is not (always) immediate.
X9. 3 hours after the first blood sugar reading, measure blood sugar & record in Chart III, line 5, Exercise Results.
X10. Subtract the Original Result line 1 from Original Result line 5. This is the toast effect without exercise Toast effect without exercise=(D5−D1)=_____.
X11. Subtract Exercise Result line 1 from Exercise Result line 5. This is the toast effect WITH exercise Toast effect with exercise=(E5−E1)=_____.
X12. Calculate the effect of exercise, by subtracting the toast effect with exercise, from that without exercise. (Step X10)−(Step X11)=effect of exercise.
X13 Recall the total insulin absorption rate, from step 20.
X14 Divide the exercise effect (Step X12) by this total insulin absorption rate, to determine the number in insulin units FEWER that will be taken before any scheduled exercise.

Apparatus for Dose Management

The present invention further provides systems, particularly computer-based systems, for performing methods of the invention.

As used herein, "a computer-based system" refers to the hardware means, software means, and data storage means used to manage dosing according to the present invention. The minimum hardware means of the computer-based systems of the present invention comprises a central processing unit (CPU), input means, output means, and data storage means. A skilled artisan can readily appreciate which of the currently available computer-based system are suitable for use in the present invention.

As stated above, the computer-based systems of the present invention comprise a data storage means having stored therein data of the present invention and the necessary hardware means and software means for supporting and implementing an analysis means. As used herein, "data storage means" refers to memory which can record data (food units, insulin units, total sugar values, sugar release rate values etc.) of the present invention, or a memory access means which can access manufactures having recorded thereon the data of the present invention. "Recorded" refers to a process for storing information on computer readable medium. A skilled artisan can readily adopt any of the presently know methods for recording information on computer readable medium.

As used herein, "analysis means" refers to one or more programs which are implemented on the computer-based system to analyze data stored within the data storage means. Analysis means are used to compare and calculate values.

One application of this embodiment provides a block diagram of a computer system that can be used to implement the present invention. The computer system includes a processor connected to a bus. Also connected to the bus are a main memory (preferably implemented as random access memory, RAM) and a variety of secondary storage memory such as a hard drive and a removable storage medium. The removable medium storage device may represent, for example, a floppy disk drive, A CD-ROM drive, a magnetic tape drive, etc. A removable storage unit (such as a floppy disk, a compact disk, a magnetic tape, etc.) containing control logic and/or data recorded therein may be inserted into the removable medium storage medium. Any suitable computer readable medium can be used. A variety of data storage structures are available to a skilled artisan for creating a computer readable medium having recorded thereon data of the present invention. The choice of the data storage structure will generally be based on the means chosen to access the stored information. In addition, a variety of data processor programs and formats can be used to store the data of the present invention on computer readable medium. Information can be represented in a word processing or spreadsheet text file, formatted in commercially-available software such as Excel, WordPerfect and MicroSoft Word, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the information of the present invention. The computer system includes appropriate software for reading the control logic and/or the data from the removable medium storage device once inserted in the removable medium storage device. A monitor can be used as connected to the bus to visualize the structure determination data.

As a result of the underlying methods described in this application, the devices depicted in FIG. 31 provide improved glucose and insulin monitoring and management.

FIG. 31(*a*) shows a screen, which is optionally activated by touch and has a touch menu. The device also optionally has dynamic touch buttons and a portion of the screen showing alerts, for example if the subject needs to take insulin or measure blood glucose or if the device is predicting an abnormally high or low level of blood glucose or insulin. The main display area in FIG. 31(*a*) depicts how a user can enter information (eg. entering the information that the user had 4 toasts). The screen may be used, for example with devices such as pocket organizers, (wireless) e-mail devices and/or cellular telephones. FIG. 31(*b*) shows an e-mail device having a screen showing icons such as the toast icon, chart/measurement icon and insulin (syringe) icon. FIG. 31(*c*) shows a cellular telephone optionally having a touch menu, dynamic touch buttons and alerts.

A glucometer (FIG. 31(*d*)) would optionally have three extra buttons added, compared to a conventional glucometer: Toasts (or other food unit value), Insulin (or mimetic) and Run. This will enable the diabetic subject to utilize the methods without having insert values in a chart or to calculate values by himself. There are optionally two modes. In a first mode, the diabetic patient enters the personal numbers on an ongoing basis. The other mode would be for the user to use the information that he or she currently has and typically after a week or two, the meter or other device described in this application would "learn" and then take over. In one example, the device relies on previously entered data to predict values for the subject.

In another embodiment, an insulin pump optionally has 3 new buttons: Toasts (or other food unit value), Glucometer Reading and Run. Alternatively, where a pump also has a built-in glucometer, it optionally has Toast (or other food unit value) and Run buttons. The methods (mathematics) in the device would control everything except the need to enter the number of Toasts (or other food unit value) eaten. This embodiment effectively creates an artificial pancreas. The location of the additional buttons mentioned above is optionally remote to each device.

Preferably the devices shown in FIGS. 31(*a*)–(*e*) have wireless connections so that all functionality is handled remotely and the system send out data (advice) through any wireless device. In one embodiment, wireless connections exist between devices such as those shown in FIG. 31 and desktop or notebook computers (or other devices), Bluetooth wireless technology is one example of wireless technology known in the art which may be used with devices and methods of the invention.

The use of software allows more detailed calculations than are typically comfortably done. An example of the method, as implemented by software, is below.

Method for Implementing DSS

As described above, the DSS method relies on accounting for the processes which affect the blood sugar level, —carbohydrate intake, exercise, and insulin injection, by frequent measurement of sugar levels and prediction of the effect of proposed intake of food or insulin injection. The prediction is accomplished by calibrating the individual's body as it responds to known quantities of food, insulin and exercise.

The calibration process requires the measurement of blood sugar levels subsequent to the introduction of known quantities of carbohydrate or insulin, usually at an interval of several hours. It is important to recognize, however, that the measurement is only showing total cumulative effect of all factors, making it necessary to disentangle the effect of the particular intake being measured from the levels which would be shown in the absence of the intake. This means that account must be taken of the total commitment for the sugar levels over the timeframe of measurement, and extraction of the difference made by the new addition.

An implementation of the DSS method requires that the superposition effect be dealt with, and that the assimilation rate for carbohydrate and insulin be defined as a function of time. The following set of algorithms and procedures has been devised in order to deal with this complex problem in a manner which is usable by the average patient with standard tools at his disposal.

Effect of Carbohydrate and Insulin Intake

Carbohydrate and insulin action on the sugar levels is known to exhibit a delay in activation after intake, then to reach a peak level of activity which is fairly constant for a period of time, and then fall off over a prolonged period after the peak levels. The amount of delay as well as the duration of the peak are a function of the type of insulin (short-term, long lasting, etc.) or carbohydrate (fast versus slow to show up in blood). The activity rate at the peak is a function of the total dosage which is ingested.

The following general function is used to describe the observed behaviour of blood sugar level as affected by carbohydrate intake:

$$s(t, d, p) = d \times b(p) \times (t - t_0)^2 e^{-\frac{(t-t_0)}{a(p)}} \quad (1)$$

where
- t is time of day
- $t_0$ is the time of application
- d is total intake
- p is the type of carbohydrate or insulin
- a(p) is the effect duration for given type divided by 7.2
- b(p) is the scaling function calculated by measurement of sugar level b(p) is determined by integration of the sugar level effect function and comparing to the measured level at a time after the intake:

$$b(p) = \frac{s(t_m, d, p) - s(t_0, d, p)}{d \times [2a^3 - e^{\frac{t_m}{a(p)}}(at_m^2 + 2a^2 t_m + 2a^3)]} \quad (2)$$

where $t_m$ is the time of measurement after introduction.

A similar form is assumed for insulin intake and exercise, except that the effect is negative on the sugar level scale.

This type of function shows the expected behaviour of sugar levels as seen in the following graphs for carbohydrate intake at 8 am and insulin injection at 8 am. The insulin curve is for a long lasting insulin variety.

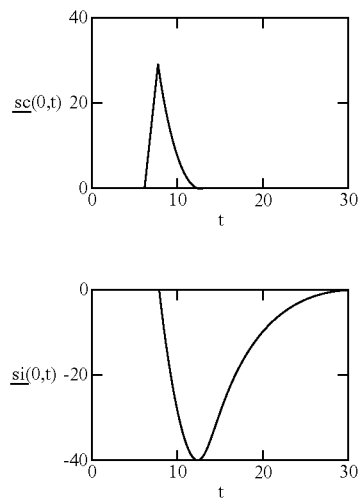

Projected Sugar Level

The combined effect of a number of intakes of carbohydrate over the course of the day and a number of insulin injections and exercise is then the sum of the functions describing each of these:

$$s(t) = s_0(t) + \sum_j (sc(j, t) + si(j, t) + se(j, t)) \quad (3)$$

where j is a counter over the number of separate intakes over the course of a day, and $s_0(t)$ is the effect of previous dosages, and is also a function of time.

An example of the calculated deviation $s(t)-s_0(t)$ as a function of time is shown in the graph for a typical day with intake of carbohydrate at 7 times during the day, 2 shots of long acting insulin in the morning and evening, and exercise in the morning and late afternoon. This shows a deviation of 29 units on the positive side and 38 units on the negative side over a period of 24 hours.

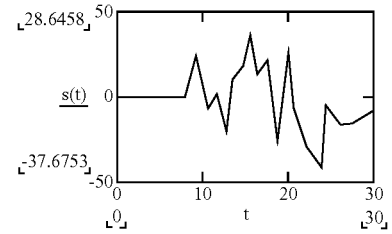

Application Method

Any implementation of the above method will preferably include the following components:

- Memory capability to maintain information about current and past intakes and insulin injections, as well as derived parameters specific to the individual
- The facility for generating calibration factors specific to the individual
- Use of the above to predict the hour by hour sugar levels as a result of the stored information and information supplied by the user
- A facility for self-correction which keeps track of the deviations of predicted values from measured values and makes adjustments for the user in order to improve future predictions
- User interface to accept information about planned intakes and display projections of status for the next period of hours to days.

The following schematic shows the process which is required to execute the method.

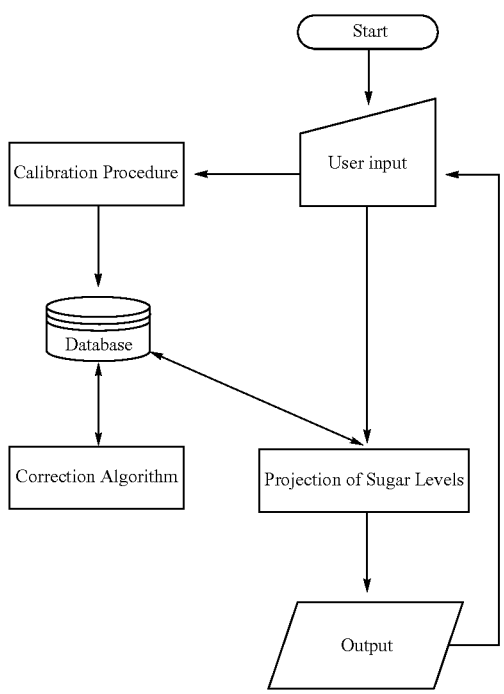

Calibration phase

In the calibration phase, careful measurements are made of the sugar levels following carbohydrate intake or insulin injection of the various types. These measurements are used in equation 2 to determine the b(p) function for each of the particular types of carbohydrate or insulin. The a(p) are generally determined from the known properties of the insulin or carbohydrate, but these can also be tuned to the behaviour within the specific individual.

Because of the effect of committed changes in sugar level from previous activity, the starting measurement should be made as late as possible after the last activity and the end point measurement should be made at several times after the activity without intervening activity. By maintaining a history of the b(p) coefficients over a long enough time, a consensus set of values can be developed for the specific individual. The use of neural networks for the purpose of including prior responses and responses which may change with time is also being investigated.

Prediction Phas

Once the a(p) and b(p) coefficients have been determined, equation 3 is used to project the impact of intake of food or insulin injection. This can be done for a planned period where the food intake is scheduled and the amount of insulin and the timing need to be determined, or can be done to evaluate the impact of a single intake on the next few hours of sugar levels.

In one method of application, the user is allowed to specify the food intake amount and timing, and then be permitted to attempt to maintain a flat variance profile by moving the timing and dosage of the insulin injection. This then gives to the user the required timing and dosage of insulin for the day.

Monitoring and Adjustment Phase

During the day, as the user enters the amount of carbohydrate ingested and timing, and the dosage and timing of insulin injected, and new sugar readings are taken, the projection is recalculated. Part of the recalculation is a determination of the variance from prior projections in order to determine correction factors for the a(p) and b(p) functions for future use.

The use of self-correcting neural net with memory would permit this adjustment phase to be an ongoing feature, and would serve to track the changes in a user's response to the food and insulin over time, as well as correcting projections which may be going off-track.

Method of Implementation

Implementing the methods of the invention, using automated tools, can range from simple automation using spreadsheet-like programs to help the patient calculate whichever protocol he chooses, to very sophisticated Neural Net programming that is self-adjusting. The devices range from web-enabled, through the PC, to handheld wireless devices. The enablement can also come in combination with existing devices such as insulin pumps and glucometers. Once continuous readout glucometers become available, our algorithm and method will provide the engine that will allow these two devices to work together.

The above algorithm enables a multitude of different implementations. However, the technology is moving fast, and tomorrow, a better device will emerge. The principle behind these implementation is always the same—using the dynamics and techniques developed in the book and the mathematical algorithm to enable automatic self-correction and advice.

The equations and methods presented above can be solved and maintained on PDA and similar devices, permitting the system to provide response to the user for projected activity in a convenient portable fashion.

The implementation would need to maintain a database of past measurements in and inputs in order to permit the tracking and adjustment which give the method its unique ability to make projections which are tested and corrected on a routine basis during the day to ensure that blood sugar deviations are kept in check.

OTHER APPLICATIONS OF THE INVENTION

The invention may also be readily adapted for dose management of other diseases, disorders or abnormal physical states by balancing levels of another administered drug with a body chemical (either a chemical produced by the body or ingested, such as food blood sugar, by the body into the blood). The methods of the invention may be readily adapted from the methods of the invention by substituting the administered drug for insulin in the methods and measuring a body chemical other than sugar. Likewise, diet may be managed by, for example, balancing carbohydrate (or other food, such as lipid or protein) or balancing calorie intake with other aspects such as the number of calories used up by the subject. Other administered drugs, such as diet drugs, may also be considered. The object may be for a healthy person to maintain a healthy body weight or improve their nutrition. The object could also be for an obese person to lose weight or for an obese person or other person at risk of diabetes to prevent or delay the onset of development of diabetes with diet management. An obese person is at greater risk of developing diabetes than a person at normal body weight. The World Health Organization (WHO) defines obesity by reference to body mass index (BMI). This is a measure derived from dividing body weight in kg by the square of height in metres. A BMI between 18.5 and 25 is normal weight. An individual is overweight with a BMI between 25 and 30. An obese subject is defined as a subject with a BMI equal to or greater than 30. The subject may also be a person whose blood glucose is higher than average for that person's age and weight (normal blood glucose may be routinely determined from medical reference sources), although not high enough that the person is diagnosed diabetic. The subject may also be a person with a genetic history of diabetes who has not yet developed diabetes.

The invention thus provides a method preventing and or delaying the onset of diabetes in a subject as well as managing and/or treating diabetes. A subject in need of such treatment is one that has diabetes or that is at risk for developing diabetes. Some people, although not diabetic, (eg obese people, whose excess weight is usually associated with insulin resistance) have poor health and a higher risk of development of type 2 diabetes. To reduce or minimize their risk of developing type 2 diabetes, the methods of the invention are used to prevent or delay the onset of type 2 diabetes. The methods of the invention may also be used to prevent or delay the onset of type 1 diabetes.

The present invention has been described in detail and with particular reference to the preferred embodiments; however, it will be understood by one having ordinary skill in the art that changes can be made without departing from the spirit and scope thereof.

All publications, patents and patent applications are incorporated by reference in their entirety to the same extent as if each individual publication, patent or patent application was specifically and individually indicated to be incorporated by reference in its entirety.

REFERENCES

Sears, Barry and Lawren, Bill. *Enter the Zone*. New York: HarperCollins, 1995
Sears, Barry. *The Age-Free Zone*. New York: HarperCollins, 1999
Brackenridge, B. P. and Dolinar, R. O. *Diabetes 101*. Minneapolis: Chronomed, 1998
Brand-Miller, Jennie, Wolever, T. M. S., Colaguiri, Stephen and Foster-Powell, Kaye. *The Glucose Revolution*. New York: Marlow, 1996
Foster-Powell, Kaye, Brand-Miller, Jennie, Wolever, T. M. S., and Colaguiri, Stephen. *The Glucose Revolution, A Pocket Guide*. New York: Marlow, 1997
Netzer, C. T. *Carbohydrate Counter*. New York: Dell, 2001
References to DCCT: The web gives myriad listings about DCCT: the following give some summary figures, and a plethora of cross-links.
Diabetes Control and Complications Trial (DCCT)
. . . What Is the DCCT?
http://www.niddk.nih.gov/health/diabetes/pubs/dcct1/dcct.htm
More Results From: www.niddk.nih.gov
The Diabetes Control and Complications Trial (DCCT)
. . . links to additional information about the DCCT.
http://www.bsc.gwu.edu/bsc/studies/dcct.html
More Results From: www.bsc.gwu.edu
More details about the DCCT
. . . More details about the DCCT . . . follow up study which may shed light on some of the unanswered questions.
http://www.faqs.org/faqs/diabetes/faq/part5/section-4.html
More Results From: www.faqs.org

I claim:
1. A method of food and insulin dose management for a diabetic subject, comprising:
providing an intended insulin unit value or an intended carbohydrate unit value representing the amount of insulin or carbohydrate intended for intake by the subject;
determining a balance value of either insulin units or carbohydrate units needed to balance with the provided unit value and maintain blood sugar in the subject in a target blood sugar range;
wherein the balance value is calculated by determining for the subject a starting blood sugar value and comparing sugar metabolism resulting from the provided unit value with an opposing sugar metabolism resulting from intended insulin or carbohydrate and thereby calculating the balance value as an amount of insulin units or carbohydrate units necessary to maintain blood sugar in the subject in a target blood sugar range; and;
wherein the sugar metabolism resulting from the provided unit value and the opposing sugar metabolism resulting from insulin or carbohydrate units are determined individually for a subject from an amount of sugar released and rate of release of sugar by food in the subject and an amount of sugar removed and rate of removal of sugar by insulin in the subject.
2. The method of claim 1, wherein the subject provides an intended insulin unit value and the method further comprises,
determining a starting blood sugar value in the subject;
determining from the intended insulin unit value i) a total sugar removal value to be removed from the blood of the subject and ii) a sugar removal rate value;
determining the balance value by determining an effective amount of carbohydrate units to be taken in by the subject to balance with the values in i) and ii) so that an ending blood sugar value in the subject is in a target blood sugar range.
3. The method of claim 2, comprising:
entering the starting blood sugar value in a timetable
determining the amount of insulin, insulin analog or insulin mimetic to be ingested as insulin units and entering the number of insulin units in the timetable;
determining the total sugar removal value to be caused by the insulin units and the sugar removal rate value per unit of time and entering in the timetable the total sugar removal value and the sugar removal rate value per unit of time;
determining the balance value as the number of balancing carbohydrate units to be administered to the subject to balance the total amount of sugar removed by the insulin units and entering the number of carbohydrate units in the timetable;
determining the total sugar release value and entering the value in the timetable;
determining the sugar release rate value per unit of time after intake of carbohydrate units and entering the sugar release rate value per unit of time in the timetable;
determining an ending blood sugar value for each unit of time and inserting the ending blood sugar value as the starting sugar value for the following unit of time.
4. The method of claim 3 wherein the timetable comprises a matrix, with one axis of the matrix having fields representing units of time and the other axis of the matrix having a plurality of fields with a field representing units selected from the group consisting of starting sugar, carbohydrate units, sugar release per unit of time, insulin units, sugar reduction value per unit of time and ending blood sugar.

5. The method of claim 1, wherein the method is performed by or directed by the subject.

6. The method of claim 1, wherein the subject provides an intended carbohydrate unit value and the method further comprises,
   determining a starting blood sugar value in the subject;
   determining from the carbohydrate unit value i) a total sugar release value and ii) a sugar release rate value;
   determining the balance value by determining an effective amount of insulin, insulin analog or insulin mimetic to administer to the subject to balance with the values in i) or ii) so that an ending blood sugar value in the subject is in a target blood sugar range.

7. The method of claim 1, further comprising i) the subject receiving food in accordance with the intended carbohydrate unit value and ii) the subject receiving insulin, insulin analog or insulin mimetic containing a number of insulin units in accordance with the balance value.

8. The method of claim 6, comprising:
   entering the starting blood sugar value in a timetable
   determining the amount of carbohydrate to be ingested as carbohydrate units and entering the number of carbohydrate units in the timetable;
   determining the total amount of sugar in the carbohydrate units and the sugar release rate value per unit of time and entering in the timetable the total amount of sugar and the sugar release rate value per unit of time;
   determining the balance value as the number of balancing insulin units to be administered to the subject to balance the total amount of sugar in the carbohydrate units and entering the number of insulin units in the timetable;
   determining the total sugar removal value and entering the value in the timetable;
   determining the sugar removal rate value per unit of time after administration of insulin, insulin analog or insulin mimetic and entering the sugar reduction rate value per unit of time in the timetable;
   determining an ending blood sugar value for each unit of time and inserting the ending blood sugar value as the starting sugar value for the following unit of time.

9. The method of claim 1, further comprising i) the subject receiving insulin, insulin analog or insulin mimetic in accordance with the intended insulin unit value and ii) the subject receiving food containing a number of carbohydrate units in accordance with the balance value.

10. The method of claim 1, wherein the carbohydrate unit comprises about 16 g of carbohydrate.

11. The method of claim 1, wherein the intended carbohydrate unit comprises toast or bread including about 16 g of carbohydrate.

12. The method of claim 1, wherein i) the subject provides a first time schedule for periodic, divided intake of the intended insulin unit value or the intended carbohydrate unit value and ii) the balance value is determined according to a second time schedule for the subject to intake insulin units or carbohydrate units needed to balance with the provided unit value and maintain blood sugar in the subject in the target blood sugar range during the time schedules.

13. The method of claim 12, further comprising determining whether the subject did intake the intended food and insulin according to the first time schedule and, if the subject did not intake the intended food and insulin, then adjusting the ending blood sugar value.

14. The method of claim 13, further comprising increasing or decreasing future insulin units or carbohydrate units so that the ending blood sugar value is in a target blood sugar range.

15. The method of claim 13, wherein if the subject did intake the intended food and insulin according to the time schedule and there is over a 25 point difference between the ending blood sugar value and the actual blood sugar value, then increasing or decreasing future insulin units or carbohydrate units so that the ending blood sugar value is in a target blood sugar range.

16. The method of claim 6, further comprising repeating the recited steps of claim 6, wherein the starting blood sugar value in the repeated step is i) determined by using the previously determined ending blood sugar level value as the starting blood sugar value or ii) determined by measuring a subject blood sugar.

17. The method of claim 16 further comprising determining the difference in actual subject blood sugar value and ending blood sugar values at a plurality of time intervals.

* * * * *